US008206710B2

(12) United States Patent
Ebel et al.

(10) Patent No.: US 8,206,710 B2
(45) Date of Patent: Jun. 26, 2012

(54) ANTI-MESOTHELIN ANTIBODIES

(75) Inventors: Wolfgang Ebel, Philadelphia, PA (US);
Luigi Grasso, Bryn Mawr, PA (US);
Nicholas C. Nicolaides, Garnett Valley, PA (US); Philip M. Sass, Audubon, PA (US); Eric Routhier, Glen Mills, PA (US)

(73) Assignee: Morphotek, Inc., Exton, PA (US)

( * ) Notice: Subject to any disclaimer, the term of this patent is extended or adjusted under 35 U.S.C. 154(b) by 363 days.

(21) Appl. No.: 12/545,369

(22) Filed: Aug. 21, 2009

(65) Prior Publication Data
US 2010/0028336 A1 Feb. 4, 2010

Related U.S. Application Data

(62) Division of application No. 11/373,546, filed on Mar. 9, 2006, now Pat. No. 7,592,426.

(60) Provisional application No. 60/660,177, filed on Mar. 10, 2005.

(51) Int. Cl.
*A61K 39/395* (2006.01)

(52) U.S. Cl. .................................... 424/133.1

(58) Field of Classification Search ........................ None
See application file for complete search history.

(56) References Cited

U.S. PATENT DOCUMENTS

| | | | |
|---|---|---|---|
| 4,694,778 A | 9/1987 | Learn et al. |
| 4,851,332 A | 7/1989 | Rettig et al. |
| 5,320,956 A | 6/1994 | Willingham et al. |
| 5,525,337 A | 6/1996 | Willingham et al. |
| 5,646,253 A | 7/1997 | Wallace et al. |
| 5,789,650 A | 8/1998 | Lonberg et al. |
| 5,798,230 A | 8/1998 | Bornkamm et al. |
| 5,817,313 A | 10/1998 | Willingham et al. |
| 5,952,484 A | 9/1999 | Wallace et al. |
| 6,083,502 A | 7/2000 | Pastan et al. |
| 6,124,106 A | 9/2000 | Wallace et al. |
| 6,146,894 A | 11/2000 | Nicolaides et al. |
| 6,153,430 A | 11/2000 | Pastan et al. |
| 6,191,268 B1 | 2/2001 | Liskay et al. |
| 6,348,195 B1 | 2/2002 | Wallace et al. |
| 6,365,410 B1 | 4/2002 | Schellenberger et al. |
| 6,602,688 B1 | 8/2003 | Opper et al. |
| 6,808,894 B1 | 10/2004 | Nicolaides et al. |
| 6,809,184 B1 | 10/2004 | Pastan et al. |
| 7,081,518 B1 | 7/2006 | Pastan et al. |
| 7,592,426 B2 | 9/2009 | Ebel et al. |
| 2002/0072093 A1 | 6/2002 | Chen et al. |
| 2003/0027177 A1 | 2/2003 | Haseltine et al. |
| 2004/0142396 A1 | 7/2004 | Scholler et al. |
| 2006/0239910 A1 | 10/2006 | Nicolaides et al. |

FOREIGN PATENT DOCUMENTS

| | | |
|---|---|---|
| EP | 0 197 435 B1 | 7/1992 |
| EP | 0 239 400 B1 | 8/1994 |
| EP | 1 258 255 A1 | 11/2002 |
| WO | WO 90/07861 A1 | 7/1990 |
| WO | WO 92/07081 A2 | 4/1992 |
| WO | WO 95/24482 A1 | 9/1995 |
| WO | WO 97/25068 A2 | 7/1997 |
| WO | WO 97/42329 A1 | 11/1997 |
| WO | WO 99/00421 A1 | 1/1999 |
| WO | WO 99/09956 A1 | 3/1999 |
| WO | WO 99/28471 | 6/1999 |
| WO | WO 00/73346 | 12/2000 |
| WO | WO 02/054856 A1 | 7/2002 |
| WO | WO 02/071928 A3 | 9/2002 |
| WO | WO 02/094879 A1 | 11/2002 |
| WO | WO 03/014322 A3 | 2/2003 |
| WO | WO 2004/009782 A3 | 1/2004 |
| WO | WO 2005/014652 A1 | 2/2005 |
| WO | WO 2006/099141 | 9/2006 |

OTHER PUBLICATIONS

Freshney (Culture of Animal Cells, A Manual of Basic Technique, Alan R. Liss, Inc., 1983, New York, p. 4).*
Dermer (Bio/Technology, 1994, 12:320).*
Gura (Science, 1997, 278:1041-1042).*
Jain (Sci. Am., 1994, 271:58-65).*
"FY2009 Product Creation Meeting, Dramatic Leap Plan 2011", Eisai Co., Ltd., Power Point Presentation, 121 pages, Dec. 18, 2009.
Alberti, S., et al., "The CA-MOv18 molecule, a cell-surface marker of human ovarian carcinomas, is anchored to the cell membrane by phosphatidylinositol", Biochem. & Biophys. Res. Commun., Sep. 28, 1990, 171(3), 1051-1055.
Alsmadi, O., et al., "Antibody-dependent cellular cytotoxicity directed against cells expressing human immunodeficiency virus type I envelope of primary or laboratory-adapted strains by human and chimpanzee monoclonal antibodies of different epitope specificities", J. of Virol., Jan. 1998, 72(1), 286-293.
Andersson, H., et al., "Comparision of the therapeutic efficacy of211At- and 131I-Labelled monoclonal antibody MOv18 in nude mice with intraperitoneal growth of human ovarian cancer", Anticancer Res., Jan.-Feb. 2001, 21(1A), 409-412.
Argani, P., et al, "Mesothelin is overexpressed in the vast majority of ductal adenocarcinomas of the pancreas: identification of a new pancreatic cancer marker by serial analysis of gene expression (SAGE)", Clinical Cancer Res., Dec. 2001, 7(12), 3862-3868.
Armstrong et al., "A phase 1 study of MORAb-009, a monoclonal antibody against mesothelin in pancreatic cancer, mesothelioma and ovarian adenocarcinoma", Journal of Clinical Oncology, 2007 ASCO Annual Meeting Proceedings Part I. vol. 25, No. 18S (Jun. 20 Supplement), 2007: 14041.
Backus, H.H.J., et al., "Folate depletion increases sensitivity of solid tumor cell lines to 5-fluorouracil and antifolates", Int. J. of Cancer, Sep. 15, 2000, 87(6), 771-778.

(Continued)

*Primary Examiner* — Sheela J Huff
(74) *Attorney, Agent, or Firm* — Woodcock Washburn, LLP

(57) ABSTRACT

This invention relates to the use of monoclonal and polyclonal antibodies that specifically bind to and become internalized by mesothelin-positive cells and also induce an immune effector activity such as antibody dependent cellular cytotoxicity. The antibodies are useful in specific delivery of pharmacologic agents to mesothelin expressing cells as well as eliciting an immune-effector activity particularly on tumor cells and precursors. The invention is also related to cells expressing the monoclonal antibodies, polyclonal antibodies, antibody derivatives, such as human, humanized, and chimeric monoclonal antibodies, antibody fragments, mammalian cells expressing the monoclonal antibodies, derivatives and fragments, and methods of treating cancer using the antibodies, derivatives and fragments.

3 Claims, 3 Drawing Sheets

OTHER PUBLICATIONS

Balint, R.F., et al., "Antibody engineering by parsimonious mutagenesis", Gene, Dec. 27, 1993, 137(1), 109-118.

Bast, R. C. et al., "Reactivity of a Monoclonal Antibody with Human Ovarian Carcinoma", J. Clin. Invest., Nov. 1981, 68, 1331-1337.

Bird, R.E., "Single-chain antigen-binding proteins", Science, Oct. 21, 1988, 242(4877), 423-442.

Boerner, P., et al., "Production of antigen-specific human monoclonal antibodies from in vitro-primed human splenocytes", J. of Immunol., Jul. 1, 1991, 147(1), 86-95.

Bowie, J.U., et al., "Deciphering the message in protein sequences: tolerance to amino acid substitutions", Science, Mar. 16, 1990, 247(4948), 1306-1310.

Brinkmann, U. et al., "Cloning and Expression of the Recombinant FAb Fragment of Monoclonal Antibody K1 that Reacts with Mesothelin Present on Mesotheliomas and Ovarian Cancers", Int. J. Cancer, May 16, 1997, 71(4), 638-644.

Campbell, I.G., et al., "Folate-binding protein is a marker for ovarian cancer", Cancer Res., Oct. 1, 1991, 51(19), 5329-5338.

Cao, D., et al., "Expression of novel markers of pancreatic ductal adenocarcinoma in pancreatic nonductal neoplasms: additional evidence of different genetic pathways", Mod. Pathol., Jun. 2005, 18(6), 752-761.

Chang, K. et al., "Characterization of the Antigen (CAK1) Recognized by Monoclonal Antibody K1 Present on Ovarian Cancers and Normal Mesothelium", Cancer Research, Jan. 1, 1992, 52, 181-186.

Chang, K. et al., "Isolation and Characterization of a Monoclonal Antibody, K1, Reactive with Ovarian Cancers and Normal Mesothelium", Int. J. Cancer, Jan. 9, 1992, 50(1), 373-381.

Chang, K., et al., "Molecular cloning of the mesothelin, a differentiation antigen present on mesothelium, mesotheliomas and ovarian cancers", Proc. Natl. Acad. Sci. USA, 1996, 93, 136-140.

Chang, K., et al., "Monoclonal antibody K1 reacts with epithelial mesothelioma but not with lung adenocarcinoma", Am J. of Surgical Pathology, Mar. 1992, 16(3), 259-268.

Chaudhary, V. K. et al., "A rapid method of cloning functional variable-region antibody genes in Escherichia coli as single-chain immunotoxins", Proc. Natl. Acad. Sci. USA, Feb. 1990, 87, 1066-1070.

Chen et al., "Enhancement and destruction of antibody function by somatic mutation: unequal occurrence is controlled by V gene combinatorial associations", EMBO J., Jun. 15, 1995, 14(12), 2784-2794.

Chowdhury, P. S. et al., "Improved Stability and Yield of a Fv-Toxin Fusion Protein by Computer Design and Protein Engineering of the Fv", J. Mol. Biol., Sep. 4, 1998, 281(5), 917-928.

Chowdhury, P. S. et al., "Improving antibody affinity by mimicking somatic hypermutation in vitro", Nature Biotechnology, Jun. 1999, 17, 568-572.

Chowdhury, P.S., et al., "Generation of high titer antisera in rabbits by DNA immunization", J. of Immunological Methods, Mar. 1, 2001, 249(1-2), 147-154.

Chowdhury, P.S., et al., "Isolation of a high-affinity stable single-chain Fv specific for mesothelin from DNA-immunized mice by phage display and construction of a recombinant immunotoxin with anti-tumor activity", Proc. Natl. Acad. Sci. USA, Jan. 20, 1998, 95(2), 669-674.

Chowdhury, P.S., et al., "Isolation of anti-mesothelin antibodies from a phage display library", Mol. Immunol., Jan. 1997, 34(1), 9-20.

Clynes R.A., et al., "Inhibitory Fc receptors modulate in vivo cytoxicity against tumor targets", Nat. Med., Apr. 2000, 6(4), 443-446.

Clynes, R., et al., "Fc receptors are required in passive and active immunity to melanoma", Proc. Natl. Acad. Sci. USA, Jan. 20, 1998, 95(2), 652-656.

Cogliati, T. et al., "Preparation and biological characterization of conjugates consisting of ricin and a tumor-specific non-internalizing MAb", Anticancer Res., Jan.-Feb. 1991, 11(1), 417-421.

Cole, S. P. C. et al., "The EBV-hybridoma technique and its application to human lung cancer", Monoclonal Antibodies and Cancer Therapy (vol. 27, UCLA Symposia on Molecular and Cellular Biology, New Series) (eds. R.A. Reisfeld and S.Sell), 1985, 77-96.

Coliva, et al., Cancer Immunol. Immunother., Dec. 2005, Epub: May 31, 2005, 54(12), 1200-1213 (Abstract).

Colnaghi, M. I. et al., "Evaluation of the Suitability of a Monoclonal Antibody Raised Against Human Ovarian Carcinoma for Therapeutic Approaches", Nucl. Med. Biol., 1989, 16(6), 633-636.

Coney, L.R., et al., "Chimeric murine-human antibodies directed against folate binding receptor are efficient mediators of ovarian carcinoma cell killing", Cancer Res., May 1, 1994, 54(9), 2448-2455.

Coney, L.R., et al., "Cloning of a tumor-associated antigen: MOV18 and MOV19 antibodies recognize a folate-binding protein", Cancer Res., Nov. 15, 1991, 51(22), 6125-6132.

Correa, "Tumor Targeting in Cancer Therapy: Internalization of Antibodies", Humana Press, Totowa, NJ, 2002, 21, 391-409.

Database Uniprot online!, Accession No. Q14859, retrieved from EBI, 1996, 1 page (abstract).

Elwood, P. C., "Molecular Cloning and Characterization of the Human Folate-binding Protein cDNA from Placenta and Malignant Tissue Culture (KB) Cells", J. Biol. Chem., Sep. 5, 1989, 264(25), 14893-14901.

Elwood, P.C., et al., "The divergent 5' termini of the α human folate receptor (hFR) mRNAs originate from two tissue-specific promoters and alternative splicing: characterization of the α hFR gene structure", Biochemistry, Feb. 11, 1997, 36(6), 1467-1478.

Franklin, W.A., et al., "New anti-lung-cancer antibody cluster 12 reacts with human folate receptors present on adenocarcinoma", Int. J. Cancer, 1994, Suppl. 8, 89-95.

Frierson, H.F., et al., "Large-scale molecular and tissue microarray analysis of mesothelin expression in common human carcinomas", Hum. Pathol., Jun. 2003, 34(6), 605-609.

Frigerio, L., et al., "Assembly, secretion, and vacuolar delivery of a hybrid immunoglobulin in plants", Plant Physiol., Aug. 2000, 123(4), 1483-1493.

Fukuda, M. et al., "Enhancement of in vitro and in vivo anti-tumor activity of anti-GD2 monoclonal antibody 220-51 against human neuroblastoma by granulocyte-macrophage colony-stimulating factor and granulocyte colony-stimulating factor", International Journal of Molecular Medicine, Oct. 1998, 2(4), 471-475.

Gallo, M. G. et al., "Cloning and Expression of the H Chain V Region of Antibody OVB3 that Reacts with Human Ovarian Cancer", The Journal of Immunology, Aug. 1, 1988, 141(3), 1034-1040.

Galmozzi, E., et al., "Exon 3 of the α folate receptor gene contains a 5' splice site which confers enhanced ovarian carcinoma specific expression", FEBS Letters, Jul. 27, 2001, 502(1-2), 31-34.

Garcia, A.A., "Salvage therapy for ovarian cancer", Curr. Oncol. Rep., Sep. 1999, 1(1), 64-70.

Garin-Chesa, P., et al., "Trophoblast and ovarian cancer antigen LK26", Am. J. of Pathol., Feb. 1993, 142(2), 557-567.

Garmestani, K. et al., "Synthesis and evaluation of a macrocyclic bifunctional chelating agent for use with bismuth radionuclides", Nucl. Med. Biol., May 2001, 28(4), 409-418.

GenPept Accession No. AAC04760, Sep. 30, 1999.

GenPept Accession No. AAC50348, Jan. 19, 1996.

GenPept Accession No. NP_005814, Jun. 10, 1999.

Greenspan, N.S., et al., "Defining epitopes: it's not as easy as it seams", Nature Biotechnology, Oct. 1999, 17(10), 936-937.

Gruner, B.A., et al., "The folate receptor as a potential therapeutic anticancer target", Investigational New Drugs, 1999, 205-219.

Gubbels, J. A. A. et al., "Mesothelin-MUC16 binding is a high affinity, N-glycan dependent interaction that facilitates peritoneal metastasis of ovarian tumors", Molecular Cancer, Oct. 26, 2006, 5(1), 50.

Güssow et al., "Humanization of monoclonal antibodies", Methods in Enzymology, 1991, 203, 99-121.

Hamilton, T. et al., "Characterization of a Human Ovarian Carcinoma Cell Line (NIH:OVCAR-3) with Androgen and Estrogen Receptors", Cancer Research, Nov. 1983, 43, 5379-5389.

Hanlon, M.H., et al., "In vitro uptake, anabolism, and cellular retention of 1843U89 and other benzoquinazoline inhibitors of thymidylate synthase", Cancer Res., Jul. 15, 1996, 56(14), 3301-3306.

Harkins, K.R., "Antibody purification methods", Basic Methods in Antibody Production and Characterization, CRC Press, Howard, G.C., et al. (Eds.), 2000, Chapter 11, 141-168.

Hassan et al., "Preclinical evaluation of MORAb-009, a chimeric antibody targeting tumor-associated mesothelin", Cancer Immunity, Dec. 19, 2007, 7, 20, 10 pages.

Hassan, R. et al., "Mesothelin targeted cancer immunotherapy", Eur. J. Cancer, Jan. 2008, Epub: Oct. 22, 2007, 44(1), 46-53.

Hassan, R., "Targeted therapy of mesothelin expressing mesotheliomas (MM), ovarian cancer (OC) and pancreatic cancer (PC)", J. of Clinical Oncology, 2004, p. 3035 (Abstract).

Hassan, R., et al., "Anti-tumor activity of K1-LysPE38QR, an immunotoxin targeting mesothelin, a cell-surface antigen overexpressed in ovarian cancer and malignant mesothelioma", J. of Immunotherapy, Jul.-Aug. 2000, 23(4), 473-479.

Hassan, R., et al., "Antitumor activity of SS(dsFv)PE38 and SS1(dsFv)PE38, recombinant antimesothelin immunotoxins against human gynecologic cancers grown in organotypic culture in vitro", Clin. Cancer Res., Nov. 2002, 8(11), 3520-3526.

Hassan, R., et al., "Mesothelin: a new target for immunotherapy", Clin. Cancer Res., Jun. 15, 2004, 10(12 pt. 1), 3937-3942.

Hassan, R., et al., "SS1(dsFv)-PE38 anti-mesothelin immunotoxin in advanced malignancies: phase I and pharmacokinetic studies of alternate-day infusion", Proc. Am. Soc. Clin. Oncol., 2002, Abstract No. 113, downloaded from the Internet on Oct. 20, 2005, 2 pages.

Hellstrom, I., et al., "Mesothelin variant 1 is released from tumor cells as a diagnostic marker", Cancer Epidemiol Biomarkers Prev., May 2006, 15(5), 1014-1020.

Ho, M. et al., "Humoral Immune Response to Mesothelin in Mesothelioma and Ovarian Cancer Patients", Clin. Cancer Res., May 15, 2005, 11(10), 3814-3820.

Holm, J., et al., "Characterization of a high-affinity folate receptor in normal and malignant human testicular tissue", Bioscience Reports, Dec. 1999, 19(6), 571-580.

Holm, J., et al., "Folate receptor of human mammary adenocarcinoma", APMIS, Jun. 1994, 102(6), 413-419.

Holm, J., et al., "Folate receptors in malignant and benign tissues of human female genital tract", Biosci. Reports, Aug. 1997, 17(4), 415-427.

Holmes, E.H., "PSMA specific antibodies and their diagnostic and therapeutic use", Exp. Opin. Invest. Drugs, Mar. 2001, 10(3), 511-519.

Hough, C.D., et al., "Coordinately up-regulated genes in ovarian cancer", Cancer Res., May 15, 2001, 61(10), 3869-3876.

Houghton, A.N., et al., "Monoclonal antibodies: potential applications to the treatment of cancer", Seminars in Oncology, Jun. 1986, 13(2), 165-179.

Howard, G.C., et al. (Eds.), "Antibody Purification Methods", Basic Methods in Antibody Production and Characterization, CRC Press, 2000, Chapter 11, 142-168.

Huang, C., et al., "Construction of representative immunoglobulin variable region cDNA libraries from human peripheral blood lymphocytes without in vitro stimulation", J. of Immunol. Methods, Aug. 9, 1991, 141(2), 227-236.

Huston, J.S., et al., "Protein engineering of antibody binding sites: recovery of specific activity in an anti-digoxin single-chain Fv analogue produced in *Escherichia coli*", Proc. Natl. Acad. Sci. USA, Aug. 1988, 85(16), 5879-5883.

Iacobuzio-Donahue, C.A., et al., "Exploration of global gene expression patterns in pancreatic adenocarcinoma using cDNA microarrays", Am. J. Pathol., Apr. 2003, 162(4), 1151-1162.

Jackman, A.L., et al., "ICI D1694, a quinazoline antifolate thymidylate synthase inhibitor that is a potent inhibitor of L1210 tumor cell growth in vitro and in vivo: a new agent for clinical study", Cancer Res., Oct. 15, 1991, 51(20), 5579-5586.

Jones, P.T., et al., "Replacing the complementarity-determining regions in a human antibody with those from a mouse", Nature, May 29-Jun. 4, 1986, 321(6069), 522-525.

Keepers, Y.P., et al., "Comparison of the sulforhodamine B protein and tetrazolium (MTT) assays for in vitro chemosensitivity testing", Eur. J. of Cancer, 1991, 27(7), 897-900.

Khazaeli, M.B., et al., "Human immune response to monoclonal antibodies", J Immunother Emphasis Tumor Immunol., Jan. 1994, 15(1), 42-52.

Kikuchi, Y. et al., "Apoptosis inducing bivalent single-chain antibody fragments against CD47 showed antitumor potency for multiple myeloma", Leuk. Res., Apr. 2005, Epub: Dec. 18, 2004, 29(4), 445-450.

Köhler, G., et al., "Continuous cultures of fused cells secreting antibody of predefined specificity", Nature, Aug. 7, 1975, 256(5517), 495-497.

Kojima, T., et al., "Molecular cloning and expression of megakaryocyte potentiating factor cDNA", J. Biol. Chem., Sep. 15, 1995, 270(37), 21984-21990.

Kozbor, D., et al., "The production of monoclonal antibodies from human lymphocytes", Immunol. Today, 1983, 4(3), 72-79.

Kreitman, R. J., et al., "Immunotoxins for targeted cancer therapy", Adv. Drug Del. Rev., Apr. 6, 1998, 31(1-2), 53-88.

Kurrasch, R. H. et al., "Characterization of a Monoclonal Antibody, OVB1, Which Binds to a Unique Determinant in Human Ovarian Carcinomas and Myeloid Cells", The Journal of Histochemistry and Cytochemistry, Jan. 1989, 37(1), 57-67.

Kusano, A. et al., "Immunocytochemical study on internalization of anti-carbohydrate monoclonal antibodies", Anticancer Res., Nov.-Dec. 1993, 13(6A), 2207-2212.

Kyriakos, R.J., et al., "The fate of antibodies bound to the surface of tumor cells in vitro", Cancer Res., Feb. 15, 1992, 52(4), 835-842.

Lacey, S. W. et al., "Complementary DNA for the Folate Binding Protein Correctly Predicts Anchoring to the Membrane by Glycosyl-Phosphatidylinositol", J. Clin. Invest, Aug. 1989, 84(2), 715-720.

Li, J., et al., "Human antibodies for immunotherapy development generated via a human B cell hybridoma technology", PNAS, May 7, 2006, Epub: Feb. 27, 2006, 103(10), 3557-3562.

Li, Q., et al., "Cytotoxic activity of the recombinant anti-mesothelin immunotoxin, SS1 (dsFv) PE38, towards tumor cell lines established from ascites of patients with peritoneal mesotheliomas", Anticancer Res., May-Jun. 2004, 24(3A), 1327-1335.

Little, M., et al., "Of mice and men: hybridoma and recombinant antibodies", Immunol. Today, Aug. 2000, 21(8), 364-370.

Marks, J. D. et al., "By-passing immunization. Human antibodies from V-gene libraries displayed on phage", J. Mol. Biol., Dec. 5, 1991, 222(3), 581-597.

Maziarz, K. M. et al., "Complete Mapping of Divergent Amino Acids Responsible for Differential Ligand Binding of Folate Receptors α and β", J. Biol. Chem., Apr. 16, 1999, 274(16), 11066-11091.

McCall, A.M., et al., "Increasing the affinity for tumor antigen enhances bispecific antibody cytotoxicity", J. of Immunol., May 15, 2001, 166(10), 6112-6117.

Miotti, S., et al., "Characterization of human ovarian carcinoma-associated antigens defined by novel monoclonal antibodies with tumor-restricted specificity", Int. J. Cancer, Mar. 15, 1987, 39(3), 297-303.

Morrison, S. L., et al., "Chimeric human antibody molecules: mouse antigen-binding domains with human constant region domains", Proc. Natl. Acad. Sci. USA, Nov. 1984, 81(21), 6851-6855.

Muminova, Z., et al., "Characterization of human mesothelin transcripts in ovarian and pancreatic cancer", BMC Cancer, May 12, 2004, 4, 19, 10 pages.

Nicolaides, N.C., et al., "A naturally occurring hPMS2 mutation can confer a dominant negative mutator phenotype", Mol. & Cell. Biol., Mar. 1998, 18(3), 1635-1641.

Nicolaides, N.C., et al., "Analysis of the 5' region of PMS2 reveals heterogeneous transcripts and a novel overlapping gene", Genomics, Sep. 20, 1995, 29(2), 329-334.

Niwa, R. et al., "Defucosylated chimeric anti-CC chemokine receptor 4 IgG1 with enhanced antibody-dependent cellular cytotoxicity shows potent therapeutic activity to T-cell leukemia and lymphoma", Cancer Res., Mar. 15, 2004, 64(6), 2127-2133.

Novocastra Laboratories Ltd., "NCL-MESO Instructions for Use", Mar. 16, 2004.

Onda, M. et al.",New Monoclonal Antibodies to Mesothelin Useful for Immunohistochemistry, Fluorescence-Activated Cell Sorting, Western Blotting, and ELISA", Clin. Cancer Res., Apr. 15, 2005, 11(16), 5840-5846.

Onda, M. et al., "Megakaryocyte Potentiation Factor Cleaved from Mesothelin Precursor is a Useful Tumor Marker in the Serum of Patients with Mesothelioma", Clin. Cancer Res., Jul. 15, 2006, 12(14), 4225-4231.

Ordóñez, N.G., "Application of mesothelin immunostaining in tumor diagnosis", Am. J. Surg. Pathol., Nov. 2003, 27(11), 1418-1428.

Ordóñez, N.G., "Value of mesothelin immunostaining in the diagnosis of mesothelioma", Mod. Pathol., Mar. 2003, 16(3), 192-197.

Orlandi, R., et al., "Cloning immunoglobulin variable domains for expression by the polymerase chain reaction", Proc. Natl. Acad. Sci. USA, May 1989, 86(10), 3833-3837.

Parsons, R., et al., "Mismatch repair deficiency in phenotypically normal human cells", Science, May 5, 1995, 268(5211), 738-740.

Pastan, I., "An NIH Career: from Bedside to Basic Research and Back", The Journal of Biological Chemistry, May 13, 2005, 280(19), 18553-18557.

Peoples, G.E., et al., "Vaccine implications of folate binding protein, a novel cytotoxic T lymphocyte-recognized antigen system in epithelial cancers", Clinical Cancer Res., Dec. 1999, 5(12), 4214-4223.

Persson, M. A. A., et al., "Generation of diverse high-affinity human monoclonal antibodies by repertoire cloning", Proc. Nat. Acad. Sci. USA, Mar. 15, 1991, 88(6), 2432-2436.

Peters, G.J., et al., "Transformation of mouse fibroblasts with the oncogenes H-ras OR trk is associated with pronounced changes in drug sensitivity and metabolism", Int. J. of Cancer, May 28, 1993, 54(3), 450-455.

Pirker, R. et al., "Enhancement of the Activity of Immunotoxins Made with Either A Chain or *Pseudomonas* Exotoxin in Human Ovarian and Epidermoid Carcinoma Cell Lines", Cancer Research, Jul. 15, 1988, 48, 3919-3923.

Poul, M.-A., et al., "Selection of tumor-specific internalizing human antibodies from phage libraries", J. of Molecular Biol., Sep. 1, 2000, 301(5), 1149-1161.

Presta, L. G., "Antibody engineering", Curr Opin Biotechnol. Aug. 1992, 3(4), 394-398.

Queen, C., et al., "A humanized antibody that binds to the interleukin 2 receptor", Proc. Nat. Acad. Sci. USA, Dec. 1989, 86(24), 10029-10033.

Rafi, I., et al., "Preclinical and phase I clinical studies with the nonclassical antifolate thymidylate synthase inhibitor nolatrexed dihydrochloride given by prolonged administration in patients with solid tumors", J. of Clin. Oncol., Mar. 1998, 16(3), 1131-1141.

Reichmann, L., et al., "Reshaping human antibodies for therapy", Nature, 1988, 332, 323-327.

Rettig, W.J., et al., "Cell-surface glycoproteins of human sarcomas: differential expression in normal and malignant tissues and cultured cells", Proc. Natl. Acad. Sci. USA, May 1988, 85(9), 3110-3114.

Rhee, M.S., et al., "Biochemical studies on PT523, a potent nonpolyglutamatable antifolate, in cultured cells", Mol. Pharmacol., Apr. 1994, 45(4), 783-791.

Ripani, E. et al., "Human Trop-2 is a tumor-associated calcium signal transducer", Int. J. Cancer, May 29, 1998, 76(5), 671-676, (Abstract).

Robinson, B. W. S. et al., "Mesothelin-family proteins and diagnosis of mesothelioma", The Lancet, Nov. 15, 2003, 362, 1612-1616.

Roitt, et al., Immunology, $4^{th}$ Ed., Mosby, Jan. 1996, pp. 7.7-7.14.

Rosowsky, A., "PT523 and other aminopterin analogs with a hemiphthaloyl-L-ornithine side chain: exceptionally tight-binding inhibitors of dihydrofolate reductase which are transported by the reduced folate carrier but cannot form polyglutamates", Curr. Med. Chem., Apr. 1999, 6(4), 329-352.

Ross, J.F., et al., "Differential regulation of folate receptor isoforms in normal and malignant tissues in vivo and in established cell lines", Cancer, May 1, 1994, 73(9), 2432-2443.

Rudikoff et al, "Single amino acid substitution altering antigen-binding specificity", PNAS, USA, Mar. 1982, 79(6), 1979-1983.

Rump, A. et al., "Binding of Ovarian Cancer Antigen CA125/MUC16 to Mesothelin Mediates Cell Adhesion", The Journal of Biological Chemistry, Mar. 5, 2004, 279(10), 9190-9198.

Sadasivan, E., et al., "Purification, properties, and immunological characterization of folate-binding proteins from human leukemia cells", Biochim. et Biophys. Acta, Jul. 16, 1987, 925(1), 36-47.

Sato, N. et al., "Pretargeted Radioimmunotherapy of Mesothelin-Expressing Cancer Using a Tetravalent Single-Chain Fv-Streptavidin Fusion Protein", J. Nucl. Med., Jul. 2005, 46(7), 1201-1209.

Scholler, N., et al., "Soluble member(s) of the mesothelin/megakaryocyte potentiating factor family are detectable in sera from patients with ovarian carcinoma", Proc. Natl. Acad. Sci. USA, Sep. 28, 1999, 96(20), 11531-11536.

Scott, A. M. et al., "Immunological effects of chimeric anti-GD3 monoclonal antibody KM871 in patients with metastatic melanoma", Cancer Immun., Feb. 22, 2005, 5(3), 1-12.

Shaw, D.R., et al., "Mesothelin: a new target for immunotherapy", Clinical Cancer Res., Dec. 15, 2004, 10(24), 8751-8753.

Shewach, D. S. et al., "Radiosensitization of human tumor cells by gemcitabine in vitro", Semin. Oncol., Aug. 1995, 22(2 Suppl 11), 68-71.

Shields, R.L., et al., "Anti-IgE monoclonal antibodies that inhibit allergen-specific histamine release", Int. Arch. Allergy Immunol., May-Jun. 1995, 107(1-3), 412-413.

Shields, R.L., et al., "High resolution mapping of the binding site on human IgG1 for FcgammaRI, FcgammaRII, FcgammaRIII, and FcRn and design of IgG1 variants with improved binding to the FcgammaR", J. of Biological Chem., Mar. 2, 200, Epub: Nov. 28, 2000, 276(9), 6591-6604.

Shih, C., et al., "LY231514, a pyrrolo[2,3-d]pyrimidine-based antifolate that inhibits multiple folate-requiring enzymes", Cancer Res., Mar. 15, 1997, 57(6), 1116-1123.

Shinkawa, T., et al., "The absence of fucose but not the presence of galactose or bisecting N-acetylglucosamine of human IgG1 complex-type oligosaccharides shows the critical role of enhancing antibody-dependent cellular cytotoxicity", J. Biological Chem., Jan. 31, 2003, Epub: Nov. 8, 2002, 278(5), 3466-3473.

Skerra, A., et al., "Assembly of a functional immunoglobulin Fv fragment in *Escherichia coli*", Science, May 20, 1988, 240(4855), 1038-1041.

Sudimack, J., et al., "Targeted drug delivery via the folate receptor", Adv. Drug Deliv. Rev., Mar. 30, 2000, 41(2), 147-162.

Sun et al., "Antitumour activity of a chimeric antibody against the leucocyte antigen CD48", Cancer Immunol. Immunther., Jan. 2000, 48(10), 595-602.

Taylor, E.C., et al., "A dideazatetrahydrofolate analogue lacking a chiral center at C-6, N-[4[2-(2-amino-3,4-dihydro-4-ox-7H-pyrrolo[2,3-d]pyrimidin-5-yl)ethyl]benzoyl]-L-glutamic acid, is an inhibitor of thymidylate synthase", J. Med. Chem., Nov. 13, 1992, 35(23), 4450-4454.

Tempest, P.R., et al., "Reshaping a human monoclonal antibody to inhibit human respiratory syncytial virus infection in vivo", Biotechnology, Mar. 1991, 9(3), 266-271.

Tomassetti, A., et al., "Isolation and biochemical characterization of the soluble and membrane forms of folate binding protein expressed in the ovarian carcinoma cell line IGOV1", FEBS Letts., Feb. 8, 1993, 317(1-2), 143-146.

Tsujimoto, M. et al., "Purification, cDNA Cloning, and Characterization of a New Serpin with Megakaryocyte Maturation Activity", The Journal of Biological Chemistry, Jun. 13, 1997, 272(24), 15373-15380.

Van Zanten Przbysz, I., et al., "cellular and humoral responses after multiple injections of unconjugated chimeric monoclonal antibody MOv18 in ovarian cancer patients: a pilot study", J. Cancer Res. Clin. Oncol., Sep. 2002, Epub: Aug. 23, 2002, 128(9), 484-492.

Van Zanten-Przybysz, I., et al., "Influence of the route of administration on targeting of ovarian cancer with the chimeric monoclonal antibody MOV18: I.V. VS. I.P.", Int. J. of Cancer, Apr. 1, 2001, 92(1), 106-114.

Veggian, R., et al., "Immunohistochemical reactivity of a monoclonal antibody prepared against human ovarian carcinoma on normal and pathological female genital tissues", Tumori, Oct. 31, 1989, 75(5), 510-513.

Velders, M.P., et al., "The impact of antigen density and antibody affinity on antibody-dependent cellular cytotoxicity: relevance for immunotherapy of carcinomas", B. J. Cancer, Aug. 1998, 78(4), 478-483.

Verhoeyen, M., et al., "Reshaping human antibodies: grafting an antilysozyme activity", Science, Mar. 25, 1988, 239(4847), 1534-1536.

Ward, E.S., et al., "Binding activities of a repertoire of single immunoglobulin variable domains secreted from *Escherichia coli*", Nature, Oct. 12, 1989, 341(2642), 544-546.

Webber, S., et al., "AG337, a novel lipophilic thymidylate synthase inhibitor: in vitro and in vivo preclinical studies", Cancer Chemother. Pharmacol., 1996, 37(6), 509-517.

Weitman, S.D., et al., "Distribution of the folate receptor GP38 in normal and malignant cell lines and tissues", Cancer Res., Jun. 15, 1992, 52(12), 3396-3401.

Wolff, E.A., et al., "Monoclonal antibody homodimers: enhanced antitumor activity in nude mice", Cancer Res., Jun. 1, 1993, 53(11), 2560-2565.

Yamaguchi, M. et al., "A Nucleotide Sequence Essential for the Function of DRE, a Common Promoter Element for *Drosophila* DNA Replication-related Genes", The Journal of Biological Chemistry, Jun. 30, 1995, 270(26), 15808-15814.

Yamaguchi, N. et al., "Characterization, Molecular Cloning and Expression of Megakaryocyte Potentiating Factor", Stem Cells, 1996, 14(Suppl 1), 62-74.

Yamaguchi, N., et al., "A novel cytokine exhibiting megakaryocyte potentiating activity from a human pancreatic tumor cell line HPC-Y5", J. Biol. Chem., Jan. 14, 1994, 269(2), 805-808.

Yang, X.-D., et al., "Eradication of established tumors by a fully human monoclonal antibody to the epidermal growth factor receptor without concomitant chemotherapy", Cancer Research, Mar. 15, 1999, 59(6), 1236-1243.

Yen, M.J. et al., "Diffuse Mesothelin Expression Correlates with Prolonged Patient Survival in Ovarian Serous Carcinoma", Clin. Cancer Res., Feb. 1, 2006, 12(3), 827-831.

Zafiropoulos, A., et al., "Induction of antigen-specific isotype switching by in vitro immunization of human naïve B lymphocytes", J. of Immunological Methods, Jan. 15, 1997, 200(1-2), 181-190.

Zhuang Zuo. et al., An efficient route to the production of a IgG-like bispecific antibody, Protein Engineering, May 2000, 13(5), 361-367.

English Translation of Japanese Patent Application No. 2008-500966: Notice of Reasons for Refusal dated Aug. 30, 2011, 4 pages.

Owens et al., "The Genetic Engineering of Monoclonal Antibodies", Journal of Immunological Methods, 1994, vol. 168, No. 2, 149-165.

Roitt et al., Immunology Illustrated (Original Book Fifth Edition), Nankodo, Feb. 10, 2000, First Edition, 71-82.

* cited by examiner

ANTI-MESOTHELIN ANTIBODIES

CROSS-REFERENCE TO RELATED APPLICATION

This application is a divisional of U.S. patent application Ser. No. 11/373,546 filed Mar. 9, 2006, now U.S. Pat. No. 7,592,426, which claims benefit of U.S. Provisional Application 60/660,177, filed Mar. 10, 2005, both of which are incorporated herein by reference in their entirety.

FIELD OF THE INVENTION

This invention relates to antibodies that specifically bind to mesothelin. In some embodiments of the invention, the antibodies are either internalized by cells expressing or bearing mesothelin ("mesothelin-positive cells") or induce an immune effector activity on mesothelin-positive cells. The antibodies of the invention are useful in specific delivery of pharmacologic agents to mesothelin-positive cells as well as in eliciting an immune effector activity on mesothelin-positive cells, for example, tumor cells and precursors. The invention is also related to polynucleotides encoding the antibodies of the invention, cells expressing the antibodies of the invention, methods of producing the antibodies of the invention, compositions of the antibodies, methods of inhibiting the growth of dysplastic cells using the antibodies, and methods of treating cancer using the antibodies.

BACKGROUND OF THE INVENTION

Pancreatic cancer is the fifth leading cause of death in the U.S. with a 5-year survival rate of less than 5%. Although radiotherapy and chemotherapy are the recommended treatments and have enjoyed some success, no current treatment effects 2-year survival for patients with locally advanced and metastatic disease (Lawrence, *Semin. Oncol.*, 22:68-71, 1995).

A difficulty that is commonly encountered when treating patients that have pancreatic as well as other cancers with cytotoxic small molecule drugs is that the cytotoxin causes toxicity to normal tissues as well as cancerous tissues. One approach to obtain higher specificity for the cancer tissue is the use of antibodies that can target specific antigens expressed in cancer cells that are not expressed or are expressed at a lower level on normal cells. These target antigens can be exploited using antibodies to specifically kill antigen-bearing tumor cells by a variety of mechanisms including inhibiting the biological activity of the antigen, eliciting an immune effector activity by complement dependent cytotoxicity (CDC) and/or antibody dependent cellular cytotoxicity (ADCC), or by delivering immuno- or radio-conjugates that, when delivered to the antigen-bearing cell, specifically kill the target cell. Finding antibodies that can specifically bind to and effectively kill antigen-bearing tumor cells has proven difficult for many cancers. This has been due in part to the inability to obtain robust tumor lysis due to either a lack of immune effector function or of efficient internalization of antibodies carrying immunotoxins. Due to the expression profile for mesothelin in pathologic tissue, there is an opportunity to obtain tumor-specific targeting for several cancer types including but not limited to pancreatic, ovarian, and lung cancer and mesothelioma.

Mesothelin is a glycosylphosphatidylinositol (GPI)-linked glycoprotein synthesized as a 69 kDa precursor and proteolytically processed into a 30 kDa $NH_2$-terminal secreted form and a 40 kDa membrane-bound form (Yamaguchi, et al. (1994) *J. Biol. Chem.* 269:805-808). Mesothelin is highly expressed on the surface of pancreatic cancers, ovarian cancers, mesotheliomas, lung cancers, and some other cancers. Its expression is limited on normal tissues, making it a potential target for cancer therapy. (Cao, et al., *Mod. Pathol.* 14:2005; Hassan, et al., *Clin. Cancer Res.* 2004 Jun. 15; 10(12 Pt 1):3937-42).

Administration of antibodies against mesothelin has been proposed as a strategy for treatment of mesothelioma as well as lung, ovarian, and pancreatic cancer. Full-length antibodies against mesothelin that can elicit a robust immune-effector activity and internalize for delivery of toxic conjugates, however, have not been previously developed.

In 1992, Chang et al. described monoclonal antibodies that recognized antigens on human ovarian carcinoma cells (Chang, et al., *Am. J. Surg. Pathol.* 1992 16:259-68). This antibody, called K1, was chemically conjugated to a truncated form of *Pseudomonas* exotoxin and found to bind mesothelin-positive cells and cancer cells. However, it was not useful as an immunotoxin conjugate due to its poor internalization ability. U.S. Pat. No. 6,083,502 describes mesothelin and uses for targeting and diagnosing mesothelin-positive cells using antibody K1.

Subsequent single chain antibodies were produced that bound with high-affinity and had potent antitumor activity on mesothelin-positive tumors as a conjugate. One such single chain antibody is SS1(scFv)-PE38 which has a high binding affinity ($K_d$ of 0.7 nM) to mesothelin. This single chain antibody is a stabilized form of the Fv in which a disulfide bond connects the light and heavy chain domains of the Fv. SS1 (scFv)-PE38 has been shown to have activity in killing tumor cells by internalization of the single chain antibody-immunotoxin complex (Hassan, et al., *Clin. Cancer Res.*, 8: 3520-6, 2002; Hassan, et al., *Proc. Am. Soc. Clin. Oncol.*, 21: 29a, 2002). Other groups have also developed antibodies that can bind to mesothelin and found overexpression of this antigen to be associated with various cancers (Scholler, et al., *Proc. Natl. Acad. Sci. U.S.A.* 1999 Sep. 28; 96(20):11531-6; Ordonez, *Am. J. Surg. Pathol.* 27:1418-28, 2003).

U.S. Pat. No. 6,809,184 describes a single chain high affinity antibody that binds to mesothelin at a different epitope than the K1 antibody. This antibody fragment was found to internalize in mesothelin-positive cells as a single chain fragment linked to an immunotoxin. The antibody was named SS1.

Attempts to develop immunoconjugated antibodies that can specifically target mesothelin have been performed with little success due to poor internalization and/or affinity (Hassan, et al., *J Immunother.* 2000 Jul.-Aug.; 23(4):473-9). This lack of internalization could be due to low affinity or poor internalization due to antibody composition and/or epitope binding. In addition, generation of the monoclonal antibody (mAb) K1 as an immunoconjugate was attempted because the unconjugated form was not cytotoxic itself (Hassan, et al., *Clin. Cancer Res.*, 10:3937-3942, 2004).

Provided herein are in-out antibodies that can internalize in mesothelin-positive cells and elicit a cytotoxic effect via immune effector activity. Also provided are antibody therapies for cancer, in particular for mesothelin-positive cancers, for example, pancreatic, ovarian, mesothelioma, and lung cancers, using antibodies that elicit a robust immune effector activity yet retain the ability to internalize and facilitate the delivery of toxins to mesothelin-positive cells.

SUMMARY OF THE INVENTION

The invention provides mesothelin-specific antibodies that alternatively elicit a robust immune-effector function or internalize in mesothelin-positive cells, referred to here as in-out mesothelin antibodies. As used herein, "in-out antibodies" ("in-out Abs") refer to antibodies that can alternatively elicit an immune effector activity and internalize within an antigen-presenting cell by binding to target antigen. Without wishing to be bound by any particular theory, it is believed that in-out Abs bind to the cell surface of an antigen-positive cell and internalize after a period of time unless engaged by immune-effector cells and/or biochemicals that are recruited to the antigen-antibody-positive cell. Methods for generating antibodies that are able to elicit an immune effector effect such antibody-dependent cellular cytotoxicity (ADCC) or complement dependent cytotoxicity (CDC) and to internalize have been previously described (Wolff, et al., *Cancer Res.* 1993 Jun. 1; 53:2560-5), however, it is not obvious that in-out antibodies can be developed against any antigen or epitope (Kusano et al., *Anticancer Res.* 1993 Nov.-Dec.; 13(6A): 2207-12). Antibodies that can target cell surface antigens that routinely internalize do not always internalize upon binding to the cell surface antigen (Cogliati et al., *Anticancer Res.* 11:417-21, 1991). Moreover, antibodies that can target cell surface antigens do not always elicit an immune effector function upon binding to the cell surface antigen (Niwa, et al., *Cancer Res.* 64:2127-33, 2004; Kikuchi, et al., *Leuk. Res.* 29:445-50, 2005; Scott, et al., *Cancer Immun. Feb.* 22; 5:3, 2005). In-out antibodies that can target mesothelin have not been described previously.

Provided herein are antibodies that bind to the cell surface antigen mesothelin and can, in the alternative, elicit an immune effector activity (e.g., ADCC or CDC) and internalize within antigen (mesothelin)-positive cells. These antibodies are useful for cancer therapy.

The invention provides antibodies that specifically bind to mesothelin wherein the antibodies are distinguished from MAb K1 in that (a) the antibodies bind with greater affinity and/or avidity than MAb K1; (b) the antibodies elicit an immune effector effect such as but not limited to ADCC or CDC; and (c) as an alternative to (b), the antibodies internalize in mesothelin-positive cells.

The invention provides antibodies that specifically bind to mesothelin wherein the antibodies are distinguished from SS1 in that (a) the antibody internalizes in mesothelin-positive cells; and (b) in the alternative, the antibodies elicit an immune effector activity, such as but not limited to ADCC or CDC. In some embodiments, the antibodies of the invention bind with a different affinity and/or avidity than SS1.

The antibodies of the invention include chimeric antibodies, including, but not limited to human-mouse chimeric antibodies. The antibodies of the invention may also be humanized antibodies. The antibodies of the invention may also be fully human antibodies. The invention also provides: hybridoma cells that express the antibodies of the invention; polynucleotides that encode the antibodies of the invention; vectors comprising the polynucleotides that encode the antibodies of the invention; and expression cells comprising the vectors of the invention, referred to as transfectomas.

The invention also provides methods of producing antibodies of the invention. In some embodiments, the methods involve a step of culturing a transfectoma or hybridoma cell that expresses an antibody of the invention. The antibody-producing cells of the invention may be bacterial, yeast, insect, or animal cells, and preferably, are mammalian cells.

The invention further provides methods of inhibiting the growth of mesothelin-positive cells, such as but not limited to, tumor or dysplastic cells associated with increased expression of mesothelin relative to normal cells, comprising administering to a subject with such cells a composition comprising an in-out antibody of the invention. The methods may be used for various malignant and dysplastic conditions, such as, but not limited to mesothelioma and pancreatic, ovarian and lung cancer. In preferred embodiments, the subjects are animals. In more preferred embodiments, the subjects are mammals. In a most preferred embodiment, the subjects are human. In some embodiments, the antibodies are conjugated to one or more chemotherapeutic agents such as, but not limited to radionuclides, toxins, and cytotoxic and cytostatic agents. In other embodiments the antibodies are used in combination with one or more chemotherapeutic agents. In-out antibodies can be administered as a single agent, as a conjugated or unconjugated antibody, or in combination with the conjugated or unconjugated forms or another therapeutic agent.

Other features and advantages of the invention will be apparent from the detailed description and examples that follow.

BRIEF DESCRIPTION OF THE DRAWINGS

FIG. 3 shows the ability of MSAb-1 linked to saporin (triangles) to kill cells in contrast to MSAb-1 unconjugated (X) while an isotype control antibody ML1 did not kill cells in conjugated or unconjugated toxin form (diamond and square, respectively). As control, cells not expressing mesothelin were used. Toxin conjugated MSAb-1 has no toxic effect in conjugated or unconjugated form on the control cells. These data support the findings that MSAb-1 internalizes in mesothelin-positive cells.

DETAILED DESCRIPTION OF ILLUSTRATIVE EMBODIMENTS

Figure 1:
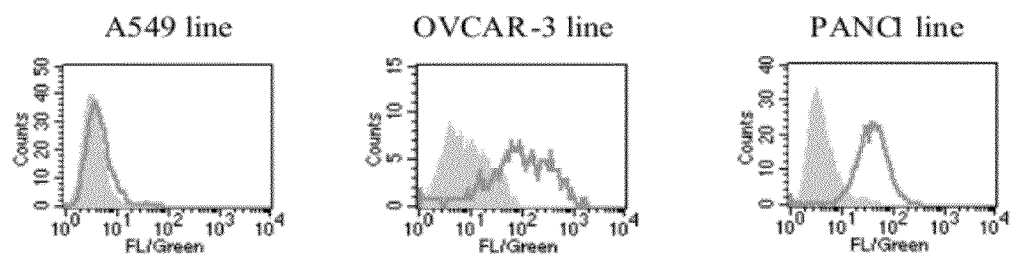
FIG. 1 shows results of FACS analysis of MSAb-1 binding to mesothelin-expressing cells (OVCAR-3-ovarian and PANC1-pancreatic cells) while no binding is observed on A549 cells. These data were confirmed by western blot analysis (not shown).

The reference works, patents, patent applications, and scientific literature, including accession numbers to GenBank database sequences that are referred to herein establish the knowledge of those with skill in the art and are hereby incorporated by reference in their entirety to the same extent as if each was specifically and individually indicated to be incorporated by reference. Any conflict between any reference cited herein and the specific teachings of this specification shall be resolved in favor of the latter. Likewise, any conflict between an art-understood definition of a word or phrase and a definition of the word or phrase as specifically taught in this specification shall be resolved in favor of the latter.

Standard reference works setting forth the general principles of recombinant DNA technology known to those of skill in the art include Ausubel et al. CURRENT PROTOCOLS 1N MOLECULAR BIOLOGY, John Wiley & Sons, New York (1998); Sambrook et al. MOLECULAR CLONING: A LABORATORY MANUAL, 2D ED., Cold Spring Harbor Laboratory Press, Plainview, N.Y. (1989); Kaufman et al., Eds., HANDBOOK OF MOLECULAR AND CELLULAR METHODS IN BIOLOGY AND MEDICINE, CRC Press, Boca Raton (1995); McPherson, Ed., DIRECTED MUTAGENESIS: A PRACTICAL APPROACH, IRL Press, Oxford (1991).

It is to be understood that this invention is not limited to particular methods, reagents, compounds, compositions or biological systems, which can, of course, vary. It is also to be understood that the terminology used herein is for the purpose of describing particular embodiments only, and is not intended to be limiting. As used in this specification and the appended claims, the singular forms "a", "an" and "the" include plural referents unless the content clearly dictates otherwise. Thus, for example, reference to "a cell" includes a combination of two or more cells, and the like.

Each range recited herein includes all combinations and sub-combinations of ranges, as well as specific numerals contained therein.

The term "about" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

The invention provides methods for decreasing or inhibiting the growth of mesothelin-positive cells (e.g., cancer cells) and the progression of neoplastic disease using in-out monoclonal antibodies that specifically bind to mesothelin. The methods of the invention may be used to modulate the growth of mesothelin-positive cells and the progression of cancer in mammals, including humans. The mesothelin-positive cells that may be inhibited include all cancer cells that have an increased expression of mesothelin in relation to normal human tissues, for example but not limited to pancreatic cancer, ovarian cancer, mesothelioma, and lung cancer cells.

Without wishing to be bound by any particular theory of operation, it is believed that the increased expression of mesothelin in cancer cells results in an increased cell surface expression of the membrane bound form on the surface of the cells. Therefore, cancer cells have an increased expression of mesothelin relative to normal tissues. Thus, the membrane-bound mesothelin is an ideal target for in-out antibody therapy in cancer.

As used herein, the term "epitope" refers to the portion of an antigen to which a monoclonal antibody specifically binds and includes, for example, conformational epitopes.

As used herein, the term "conformational epitope" refers to a discontinuous epitope formed by a spatial relationship between amino acids of an antigen other than a continuous or unbroken series of amino acids.

As used herein, the term "immune effector activity" refers to an antibody that can kill cells by antibody dependent cellular cytotoxicity (ADCC) or complement dependent cytotoxicity (CDC).

As used herein, the term "in-out antibody" refers to an antibody that can, in the alternative, elicit an immune-effector activity and internalize within the cell by binding to target antigen.

As used herein, the phrase "in the alternative" when referring to the ability of an antibody to internalize or elicit an immune effector activity means that the antibody has the ability to both internalize and elicit an immune effector activity but cannot do both simultaneously.

As used herein, the term "inhibition of growth of dysplastic cells in vitro" means a decrease in the number of tumor cells in culture by about 5%, preferably about 10%, more preferably about 20%, more preferably about 30%, more preferably about 40%, more preferably about 50%, more preferably about 60%, more preferably about 70%, more preferably about 80%, more preferably about 90%, and most preferably about 100%. In vitro inhibition of tumor cell growth may be measured by assays known in the art, for example, the GEO cell soft agar assay.

As used herein, the term "inhibition of growth of dysplastic cells in vivo" means a decrease in the number of tumor cells, in an animal, by about 5%, preferably about 10%, more preferably about 20%, more preferably about 30%, more preferably about 40%, more preferably about 50%, more preferably about 60%, more preferably about 70%, more preferably about 80%, more preferably about 90%, and most preferably about 100%. In vivo modulation of tumor cell growth may be measured by assays known in the art, for example but not limited to using the Response Evaluation Criteria in Solid Tumors (RECIST) parameters (available online through the National Cancer Institute Cancer Therapy Evaluation Program).

As used herein, "dysplastic cells" refers to cells that exhibit abnormal growth properties, such as but not limited to growth in soft agar, lack of contact inhibition, failure to undergo cell cycle arrest in the absence of serum, and formation of tumors when injected into immune-compromised mice. Dysplastic cells include, but are not limited to tumors, hyperplasia, and the like.

The term "preventing" refers to decreasing the probability that an organism contracts or develops an abnormal condition.

The term "treating" refers to having a therapeutic effect and at least partially alleviating or abrogating an abnormal condition in the organism. Treating includes inhibition of tumor growth, maintenance of inhibited tumor growth, and induction of remission.

"Therapeutic effect" refers to the reduction, elimination, or prevention of a disease or abnormal condition, symptoms thereof, or side effects thereof in the subject. "Effective amount" refers to an amount necessary to produce a desired effect. A "therapeutically effective amount" means the amount that, when administered to a subject for treating a disease, condition or disorder, is sufficient to effect treatment for that disease. A therapeutic effect relieves to some extent one or more of the symptoms of the abnormal condition. In reference to the treatment of abnormal conditions, a therapeutic effect can refer to one or more of the following: (a) an increase or decrease in the proliferation, growth, and/or differentiation of cells; (b) inhibition (i.e., slowing or stopping) of growth of tumor cells in vivo (c) promotion of cell death; (d) inhibition of degeneration; (e) relieving to some extent one or more of the symptoms associated with the abnormal condition; and (f) enhancing the function of a population of cells. The antibodies described herein effectuate the therapeutic effect alone or in combination with conjugates or additional components of the compositions of the invention.

As used herein, the term "inhibits the progression of cancer" refers to an activity of a treatment that slows the modulation of neoplastic disease toward end-stage cancer in relation to the modulation toward end-stage disease of untreated cancer cells.

As used herein, the term "neoplastic disease" refers to a condition marked by abnormal proliferation of cells of a tissue.

As used herein the term "biomolecule" refers to any molecule that can be conjugated to, coadministered with, administered before or after administering the antibody, or otherwise used in association with the antibody of the invention.

Biomolecules include, but are not limited to, enzymes, proteins, peptides, amino acids, nucleic acids, lipids, carbohydrates, and fragments, homologs, analogs, or derivatives, and combinations thereof. Examples of biomolecules include but are not limited to interleukin-2, interferon alpha, interferon beta, interferon gamma, rituxan, zevalin, herceptin, erbitux, and avastin. The biomolecules can be native, recombinant, or synthesized, and may be modified from their native form with, for example, glycosylations, acetylations, phosphorylations, myristylations, and the like. The term biomolecule as it is used herein is not limited to naturally occurring molecules, and includes synthetic molecules having no biological origin.

As used herein, the term "cytotoxic" or "cytostatic" agent refers to an agent that reduces the viability or proliferative potential of a cell. Cytotoxic or cytostatic agents can function in a variety of ways to reduce cell viability or proliferation, for example, but not by way of limitation, by inducing DNA damage, inducing cell cycle arrest, inhibiting DNA synthesis, inhibiting transcription, inhibiting translation or protein synthesis, inhibiting cell division, or inducing apoptosis. As used herein, the term "chemotherapeutic agent" refers to cytotoxic, cytostatic, and antineoplastic agents that preferentially kill, inhibit the growth of, or inhibit the metastasis of neoplastic cells or disrupt the cell cycle of rapidly proliferating cells. Specific examples of chemotherapeutic agents include, but are not limited to, radionuclides, pokeweed antiviral protein, abrin, ricin and each of their A chains, altretamine, actinomycin D, plicamycin, puromycin, gramicidin D, doxorubicin, colchicine, cytochalasin B, cyclophosphamide, emetine, maytansine, amsacrine, cisplastin, etoposide, etoposide orthoquinone, teniposide, daunorubicin, gemcitabine, doxorubicin, mitoxantraone, bisanthrene, Bleomycin, methotrexate, vindesine, adriamycin, vincristine, vinblastine, BCNU, taxol, tarceva, avastin, mitomycin, modified *Pseudomonas* enterotoxin A, calicheamicin, 5-fluorouracil, cyclophosphamide and certain cytokines such as TNF-alpha and TNF-beta.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence with respect to the expression product, but not with respect to actual probe sequences.

"Recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all.

The phrase "nucleic acid" or "polynucleotide sequence" refers to a single or double-stranded polymer of deoxyribonucleotide or ribonucleotide bases read from the 5' to the 3' end. Nucleic acids can also include modified nucleotides that permit correct read through by a polymerase and do not alter expression of a polypeptide encoded by that nucleic acid, including, for example, conservatively modified variants.

"Polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymers. Polypeptides of the invention, including antibodies of the invention, include conservatively modified variants. One of skill will recognize that substitutions, deletions or additions to a nucleic acid, peptide, polypeptide, or protein sequence which alter, add or delete a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention. The following eight groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (33). The term "conservative substitution" also includes the use of a substituted amino acid in place of an unsubstituted parent amino acid provided that such a polypeptide also displays the requisite binding activity.

"Amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. "Amino acid analog" refers to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones but retain the same basic chemical structure as a naturally occurring amino acid. "Amino acid mimetic" refers to a chemical compound having a structure that is different from the general chemical structure of an amino acid but that functions in a manner similar to a naturally occurring amino acid.

Amino acids can be referred to herein by either their commonly known three letter symbols or by the one-letter symbols recommended by the IUPAC-IUB Biochemical Nomenclature Commission (see Table 1 below). Nucleotides, likewise, can be referred to by their commonly accepted single-letter codes.

TABLE 1

| SYMBOL | | |
|---|---|---|
| 1-Letter | 3-Letter | AMINO ACID |
| Y | Tyr | L-tyrosine |
| G | Gly | L-glycine |
| F | Phe | L-phenylalanine |
| M | Met | L-methionine |
| A | Ala | L-alanine |
| S | Ser | L-serine |
| I | Ile | L-isoleucine |
| L | Leu | L-leucine |
| T | Thr | L-threonine |
| V | Val | L-valine |
| P | Pro | L-proline |
| K | Lys | L-lysine |
| H | His | L-histidine |
| Q | Gln | L-glutamine |
| E | Glu | L-glutamic acid |
| W | Trp | L-tryptophan |
| R | Arg | L-arginine |
| D | Asp | L-aspartic acid |
| N | Asn | L-asparagine |
| C | Cys | L-cysteine |

It should be noted that all amino acid sequences are represented herein by formulae whose left to right orientation is in the conventional direction of amino-terminus to carboxy-terminus.

As used herein, the term "in vitro" or "ex vivo" refers to an artificial environment and to processes or reactions that occur within an artificial environment, for example, but not limited to, test tubes and cell cultures. The term "in vivo" refers to a natural environment (e.g., an animal or a cell) and to processes or reactions that occur within a natural environment.

"Pharmaceutically acceptable," "physiologically tolerable" and grammatical variations thereof, as they refer to compositions, carriers, diluents and reagents, are used interchangeably and represent that the materials are capable of administration to or upon a human without the production of undesirable physiological effects to a degree that would prohibit administration of the composition.

The term "pharmaceutically acceptable carrier" refers to reagents, excipients, cells, compounds, materials, compositions, and/or dosage forms which are, within the scope of sound medical judgment, suitable for use in contact with the tissues of human beings and animals without excessive toxicity, irritation, allergic response, or other complication commensurate with a reasonable benefit/risk ratio. As described in greater detail herein, pharmaceutically acceptable carriers suitable for use in the present invention include gases, liquids, and semi-solid and solid materials.

Except when noted, "subject" or "patient" are used interchangeably and refer to mammals such as human patients and non-human primates, as well as experimental animals such as rabbits, dogs, cats, rats, mice, and other animals. Accordingly, "subject" or "patient" as used herein means any mammalian patient or subject to which the compositions of the invention can be administered. In some embodiments of the present invention, the patient will be suffering from an infectious or inflammatory disease. In some embodiments of the present invention, the patient will have been diagnosed with cancer. In an exemplary embodiment of the present invention, to identify candidate patients for treatment according to the invention, accepted screening methods are employed to determine the status of an existing disease or condition in a subject or risk factors associated with a targeted or suspected disease or condition. These screening methods include, for example, examinations to determine whether a subject is suffering from an infectious disease, an inflammatory disease, or cancer. These and other routine methods allow the clinician to select subjects in need of therapy.

"Therapeutic compound" as used herein refers to a compound useful in the prophylaxis or treatment of a disease or condition such as cancer.

"Concomitant administration," "concurrent administration," or "co-administration" as used herein includes administration of the active agents (e.g., MAbs, chemotherapeutic agents, biomolecules), in conjunction or combination, together, or before or after each other. The multiple agent(s) may be administered by the same or by different routes, simultaneously or sequentially, as long as they are given in a manner sufficient to allow all agents to achieve effective concentrations at the site of action. A person of ordinary skill in the art would have no difficulty determining the appropriate timing, sequence, and dosages of administration for particular drugs and compositions of the present invention.

"Immunoglobulin" or "antibody" is used broadly to refer to both antibody molecules and a variety of antibody-derived molecules and includes any member of a group of glycoproteins occurring in higher mammals that are major components of the immune system. The term "antibody" is used in the broadest sense and specifically covers monoclonal antibodies, antibody compositions with polyepitopic specificity, bispecific antibodies, diabodies, and single-chain molecules, as well as antibody fragments (e.g., Fab, F(ab')2, and Fv), so long as they exhibit the desired biological activity. An immunoglobulin molecule includes antigen binding domains, which each include the light chains and the end-terminal portion of the heavy chain, and the Fc region, which is necessary for a variety of functions, such as complement fixation. There are five classes of immunoglobulins wherein the primary structure of the heavy chain, in the Fc region, determines the immunoglobulin class. Specifically, the alpha, delta, epsilon, gamma, and mu chains correspond to IgA, IgD, IgE, IgG and IgM, respectively. As used herein "immunoglobulin" or "antibody" includes all subclasses of alpha, delta, epsilon, gamma, and mu and also refers to any natural (e.g., IgA and IgM) or synthetic multimers of the four-chain immunoglobulin structure. Antibodies non-covalently, specifically, and reversibly bind an antigen. The term "monoclonal antibody" as used herein refers to an antibody obtained from a population of substantially homogeneous antibodies, i.e., the individual antibodies comprising the population are identical except for possible naturally occurring mutations that can be present in minor amounts. For example, monoclonal antibodies may be produced by a single clone of antibody-producing cells. Unlike polyclonal antibodies, monoclonal antibodies are monospecific (e.g., specific for a single epitope of a single antigen). The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention can be made by the hybridoma method first described by Kohler et al., *Nature*, 256: 495, 1975, or can be made by recombinant DNA methods. The "monoclonal antibodies" can also be isolated from phage antibody libraries using the techniques described in Marks et al., *J. Mol. Biol.*, 222: 581-597, 1991, for example.

Antibody-derived molecules comprise portions of intact antibodies that retain antigen-binding specificity, and comprise, for example, at least one variable region (either a heavy chain or light chain variable region). Antibody-derived molecules, for example, include molecules such as Fab fragments, Fab' fragments, F(ab')2 fragments, Fd fragments, F(v)

fragments, Fabc fragments, Fd fragments, Fabc fragments, Sc antibodies (single chain antibodies), diabodies, individual antibody light chains, individual antibody heavy chains, chimeric fusions between antibody chains and other molecules, heavy chain monomers or dimers, light chain monomers or dimers, dimers consisting of one heavy and one light chain, and the like. All classes of immunoglobulins (e.g., IgA, IgD, IgE, IgG and IgM) and subclasses thereof are included.

Antibodies can be labeled/conjugated to toxic or non-toxic moieties. Toxic moieties include, for example, bacterial toxins, viral toxins, radioisotopes, and the like. Antibodies can be labeled for use in biological assays (e.g., radioisotope labels, fluorescent labels) to aid in detection of the antibody. Antibodies can also be labeled/conjugated for diagnostic or therapeutic purposes, e.g., with radioactive isotopes that deliver radiation directly to a desired site for applications such as radioimmunotherapy (Garmestani et al., *Nucl. Med. Biol.,* 28: 409, 2001), imaging techniques and radioimmunoguided surgery or labels that allow for in vivo imaging or detection of specific antibody/antigen complexes. Antibodies may also be conjugated with toxins to provide an immunotoxin (see, Kreitman, R. J. *Adv. Drug Del. Rev.,* 31: 53, 1998).

With respect to antibodies, the term, "immunologically specific" refers to antibodies that bind to one or more epitopes of a protein of interest, but which do not substantially recognize and bind other molecules in a sample containing a mixed population of antigenic biological molecules.

"Chimeric" or "chimerized" antibodies (immunoglobulins) refer to antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (Morrison et al., *Proc. Natl. Acad. Sci. U.S.A.,* 81: 6851-6855, 1984).

"Humanized" forms of non-human (e.g., murine) antibodies are chimeric immunoglobulins, immunoglobulin chains or fragments thereof (such as Fv, Fab, Fab', F(ab')2 or other antigen-binding subsequences of antibodies) which contain minimal sequence derived from non-human immunoglobulin. For the most part, humanized antibodies are human immunoglobulins (recipient antibody) in which residues from a complementary-determining region (CDR) of the recipient are replaced by residues from a CDR of a non-human species (donor antibody) such as mouse, rat or rabbit having the desired specificity, affinity, and capacity. In some instances, Fv framework region (FR) residues of the human immunoglobulin are replaced by corresponding non-human residues. Furthermore, humanized antibodies can comprise residues which are found neither in the recipient antibody nor in the imported CDR or framework sequences. These modifications are made to further refine and optimize antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin sequence. The humanized antibody optimally also will comprise at least a portion of an immunoglobulin constant region (Fc), typically that of a human immunoglobulin. For further details, see Jones et al., *Nature,* 321: 522-525, 1986; Reichmann et al., *Nature,* 332: 323-329, 1988; Presta, *Curr. Op. Struct. Biol.,* 2: 593-596, 1992.

"Fully human" refers to an immunoglobulin, such as an antibody, where the whole molecule is of human origin or consists of an amino acid sequence identical to a human form of the antibody.

"Hybridoma" refers to the product of a cell-fusion between a cultured neoplastic lymphocyte and a primed B- or T-lymphocyte which expresses the specific immune potential of the parent cell.

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein. In describing and claiming the present invention, the following terminology will be used.

Various patents and other publications are cited herein and throughout the specification, each of which is incorporated by reference herein in its entirety.

Antibodies

The in-out antibodies of the invention specifically bind mesothelin and exhibit, in the alternative, the ability to induce an immune effector activity and the ability to internalize in mesothelin-positive cells. In some embodiments, the antibodies bind to the same epitope as mAb K1 or SS1. In other embodiments, the antibodies bind to an epitope other than that bound by mAb K1 or SS1.

Antibodies suitable for use in the method of the invention, include, for example, monoclonal or polyclonal antibodies, fully human antibodies, human antibody homologs, humanized antibody homologs, chimeric antibodies, singles chain antibodies, chimeric antibody homologs, and monomers or dimers of antibody heavy or light chains or mixtures thereof. The antibodies of the invention may include intact immunoglobulins of any isotype including types IgA, IgG, IgE, IgD, IgM (as well as subtypes thereof). The light chains of the immunoglobulin may be kappa or lambda.

The in-out antibodies of the invention include portions of intact antibodies that retain antigen-binding specificity, for example, Fab fragments, Fab' fragments, F(ab')2 fragments, F(v) fragments, heavy chain monomers or dimers, light chain monomers or dimers, dimers consisting of one heavy and one light chain, and the like. Thus, antigen binding fragments, as well as full-length dimeric or trimeric polypeptides derived from the above-described antibodies are themselves useful for exhibiting in-out activity.

Chimeric antibodies may be produced by recombinant DNA technology in which all or part of the hinge and constant regions of an immunoglobulin light chain, heavy chain, or both, have been substituted for the corresponding regions from another animal's immunoglobulin light chain or heavy chain. In this way, the antigen-binding portion of the parent monoclonal antibody is grafted onto the backbone of another species' antibody. One approach, described in EP 0239400 to Winter et al. describes the substitution of one species' complementarity determining regions (CDRs) for those of another species, such as substituting the CDRs from human heavy and light chain immunoglobulin variable region domains with CDRs from mouse variable region domains. These altered antibodies may subsequently be combined with human immunoglobulin constant regions to form antibodies that are human except for the substituted murine CDRs which are specific for the antigen. Methods for grafting CDR regions of antibodies may be found, for example in Riechmann et al. (1988) *Nature* 332:323-327 and Verhoeyen et al., (1988) *Science* 239:1534-1536.

Humanized antibodies are produced by recombinant DNA technology, in which at least one of the amino acids of a human immunoglobulin light or heavy chain that is not required for antigen binding has been substituted for the corresponding amino acid from a nonhuman mammalian immunoglobulin light or heavy chain. For example, if the immunoglobulin is a mouse monoclonal antibody, at least one amino acid that is not required for antigen binding is substituted using the amino acid that is present on a corresponding human antibody in that position. Without wishing to be bound by any particular theory of operation, it is believed that the "humanization" of the monoclonal antibody inhibits human immunological reactivity against the foreign immunoglobulin molecule.

As a non-limiting example, a method of performing complementarity determining region (CDR) grafting may be performed by sequencing the mouse heavy and light chains of the antibody of interest that binds to the target antigen (e.g., mesothelin) and genetically engineering the CDR DNA sequences and imposing these amino acid sequences to corresponding human V regions by site-directed mutagenesis. Human constant region gene segments of the desired isotype are added, and the "humanized" heavy and light chain genes are co-expressed in mammalian cells to produce soluble humanized antibody. A typical expression cell is a Chinese Hamster Ovary (CHO) cell. Suitable methods for creating the chimeric antibodies may be found, for example, in Jones et al. (1986) *Nature* 321:522-525; Riechmann (1988) *Nature* 332:323-327; Queen et al. (1989) *Proc. Nat. Acad. Sci. USA* 86:10029; and Orlandi et al. (1989) *Proc. Natl. Acad. Sci. USA* 86:3833.

Queen et al. (1989) *Proc. Nat. Acad. Sci. USA* 86:10029-10033 and WO 90/07861 describe the preparation of a humanized antibody. Human and mouse variable framework regions were chosen for optimal protein sequence homology. The tertiary structure of the murine variable region was computer-modeled and superimposed on the homologous human framework to show optimal interaction of amino acid residues with the mouse CDRs. This led to the development of antibodies with improved binding affinity for antigen (which is typically decreased upon making CDR-grafted chimeric antibodies). Alternative approaches to making humanized antibodies are known in the art and are described, for example, in Tempest (1991) *Biotechnology* 9:266-271.

"Single chain antibodies" refer to antibodies formed by recombinant DNA techniques in which immunoglobulin heavy and light chain fragments are linked to the Fv region via an engineered span of amino acids. Various methods of generating single chain antibodies are known, including those described in U.S. Pat. No. 4,694,778; Bird (1988) *Science* 242:423-442; Huston et al. (1988) *Proc. Natl. Acad. Sci. USA* 85:5879-5883; Ward et al. (1989) *Nature* 334:54454; Skerra et al. (1988) *Science* 242:1038-1041.

The antibodies of the invention include derivatives that are modified, e.g., by the covalent attachment of any type of molecule to the antibody such that covalent attachment does not prevent the antibody from binding to its epitope. Examples of suitable derivatives include, but are not limited to fucosylated antibodies and fragments, glycosylated antibodies and fragments, acetylated antibodies and fragments, pegylated antibodies and fragments, phosphorylated antibodies and fragments, and amidated antibodies and fragments. The antibodies and derivatives thereof of the invention may themselves be derivatized by known protecting/blocking groups, proteolytic cleavage, linkage to a cellular ligand or other proteins, and the like. In some embodiments of the invention, at least one heavy chain of the antibody is fucosylated. In some embodiments, the fucosylation is N-linked. In some preferred embodiments, at least one heavy chain of the antibody comprises a fucosylated, N-linked oligosaccharide.

The antibodies of the invention include variants having single or multiple amino acid substitutions, deletions, additions, or replacements that retain the biological properties (e.g., internalization, binding affinity or avidity, or immune effector activity) of the antibodies of the invention. The skilled person can produce variants having single or multiple amino acid substitutions, deletions, additions or replacements. These variants may include, inter alia: (a) variants in which one or more amino acid residues are substituted with conservative or nonconservative amino acids, (b) variants in which one or more amino acids are added to or deleted from the polypeptide, (c) variants in which one or more amino acids include a substituent group, and (d) variants in which the polypeptide is fused with another peptide or polypeptide such as a fusion partner, a protein tag or other chemical moiety, that may confer useful properties to the polypeptide, such as, for example, an epitope for an antibody, a polyhistidine sequence, a biotin moiety and the like. Antibodies of the invention may include variants in which amino acid residues from one species are substituted for the corresponding residue in another species, either at the conserved or nonconserved positions. In another embodiment, amino acid residues at nonconserved positions are substituted with conservative or nonconservative residues. The techniques for obtaining these variants, including genetic (suppressions, deletions, mutations, etc.), chemical, and enzymatic techniques, are known to the person having ordinary skill in the art. Antibodies of the invention also include antibody fragments. A "fragment" refers to polypeptide sequences which are preferably at least about 40, more preferably at least to about 50, more preferably at least about 60, more preferably at least about 70, more preferably at least about 80, more preferably at least about 90, and more preferably at least about 100 amino acids in length, and which retain some biological activity or immunological activity of the full-length sequence, for example, mesothelin binding affinity or avidity, the ability to internalize, and immune effector activity.

The invention also encompasses fully human antibodies such as those derived from peripheral blood mononuclear cells of patients having mesothelin-positive cancer cells, for example, ovarian cancer, lung cancer, mesothelioma, or pancreatic cancer patients. Such cells may be fused with myeloma cells, for example, to form hybridoma cells producing fully human antibodies against mesothelin.

In preferred embodiments of the invention, the antibody comprises a heavy chain comprising an amino acid sequence of SEQ ID NO:2, SEQ ID NO:6, or SEQ ID NO:10:

```
SEQ ID NO 2:
MSAb-1 heavy chain amino acid sequence
MGWSCIILFLVATATGVHSQVQLQQSGPELEKPGASVKISCKASGYSFTG
YTMNWVKQSHGKSLEWIGLITPYNGASSYNQKFRGKATLTVDKSSSTAYM
DLLSLTSEDSAVYFCARGGYDGRGFDYWGSGTPVTVSSASTKGPSVFPLA
PSSKSTSGGTAALGCLVKDYFPEPVTVSWNSGALTSGVHTFPAVLQSSGL
YSLSSVVTVPSSSLGTQTYICNVNHKPSNTKVDKKVEPKSCDKTHTCPPC
PAPELLGGPSVFLFPPKPKDTLMISRTPEVTCVVVDVSHEDPEVKFNWYV
DGVEVHNAKTKPREEQYNSTYRVVSVLTVLHQDWLNGKEYKCKVSNKALP
APIEKTISKAKGQPREPQVYTLPPSRDELTKNQVSLTCLVKGFYPSDIAV
EWESNGQPENNYKTTPPVLDSDGSFFLYSKLTVDKSRWQQGNVFSCSVMH
EALHNHYTQKSLSLSPGK*

SEQ ID NO 6
MSAb-2 heavy chain amino acid
MGWSCIILFLVATATGVHSQVQLVQSGAEVKKPGASVKVSCKASGYSFTG
```

```
YTMNWVRQAPGQGLEWMGLITPYNGASSYNQKFRGRVTMTRDTSTSTVYM
ELSSLRSEDTAVYYCARGGYDGRGFDYWGSGTPVTVSSASTKGPSVFPLA
PSSKSTSGGTAALGCLVKDYFPEPVTVSWNSGALTSGVHTFPAVLQSSGL
YSLSSVVTVPSSSLGTQTYICNVNHKPSNTKVDKKVEPKSCDKTHTCPPC
PAPELLGGPSVFLFPPKPKDTLMISRTPEVTCVVVDVSHEDPEVKFNWYV
DGVEVHNAKTKPREEQYNSTYRVVSVLTVLHQDWLNGKEYKCKVSNKALP
APIEKTISKAKGQPREPQVYTLPPSRDELTKNQVSLTCLVKGFYPSDIAV
EWESNGQPENNYKTTPPVLDSDGSFFLYSKLTVDKSRWQQGNVFSCSVMH
EALHNHYTQKSLSLSPGK*

SEQ ID NO: 10
MSAb-3 heavy chain amino acid sequence
MGWSCIILFLVATATGVHSQVQLVQSGAEVKKPGASVKVSCKASGYSFTG
YTMNWVKQAPGQGLEWIGLITPYNGASSYNQKFRGKATMTRDTSTSTVYM
ELSSLRSEDTAVYFCARGGYDGRGFDYWGSGTPVTVSSASTKGPSVFPLA
PSSKSTSGGTAALGCLVKDYFPEPVTVSWNSGALTSGVHTFPAVLQSSGL
YSLSSVVTVPSSSLGTQTYICNVNHKPSNTKVDKKVEPKSCDKTHTCPPC
PAPELLGGPSVFLFPPKPKDTLMISRTPEVTCVVVDVSHEDPEVKFNWYV
DGVEVHNAKTKPREEQYNSTYRVVSVLTVLHQDWLNGKEYKCKVSNKALP
APIEKTISKAKGQPREPQVYTLPPSRDELTKNQVSLTCLVKGFYPSDIAV
EWESNGQPENNYKTTPPVLDSDGSFFLYSKLTVDKSRWQQGNVFSCSVMH
EALHNHYTQKSLSLSPGK*.
```

In some preferred embodiments, the heavy chain of the antibody is encoded by a nucleotide sequence comprising SEQ ID NO:1, SEQ ID NO:5, or SEQ ID NO:9:

```
SEQ. ID. NO. 1:
MSAb-1 heavy chain nucleotide sequence
ATGGGATGGAGCTGTATCATCCTCTTCTTGGTAGCAACAGCTACAGGTGT
ACACAGCCAGGTACAACTGCAGCAGTCTGGGCCTGAGCTGGAGAAGCCTG
GCGCTTCAGTGAAGATATCCTGCAAGGCTTCTGGTTACTCATTCACTGGC
TACACCATGAACTGGGTGAAGCAGAGCCATGGAAAGAGCCTTGAGTGGAT
TGGACTTATTACTCCTTACAATGGTGCTTCTAGCTACAACCAGAAGTTCA
GGGGCAAGGCCACATTAACTGTAGACAAGTCATCCAGCACAGCCTACATG
GACCTCCTCAGTCTGACATCTGAAGACTCTGCAGTCTATTTCTGTGCAAG
GGGGGGTTACGACGGGAGGGGTTTTGACTACTGGGGATCCGGGACCCCGG
TCACCGTCTCCTCAGCCTCCACCAAGGGCCCATCGGTCTTCCCCCTGGCA
CCCTCCTCCAAGAGCACCTCTGGGGGCACAGCGGCCCTGGGCTGCCTGGT
CAAGGACTACTTCCCCGAACCGGTGACGGTGTCGTGGAACTCAGGCGCCC
TGACCAGCGGCGTGCACACCTTCCCGGCTGTCCTACAGTCCTCAGGACTC
TACTCCCTCAGCAGCGTGGTGACCGTGCCCTCCAGCAGCTTGGGCACCCA
GACCTACATCTGCAACGTGAATCACAAGCCCAGCAACACCAAGGTGGACA
AGAAAGTTGAGCCCAAATCTTGTGACAAAACTCACACATGCCCACCGTGC
CCAGCACCTGAACTCCTGGGGGGACCGTCAGTCTTCCTCTTCCCCCCAAA
ACCCAAGGACACCCTCATGATCTCCCGGACCCCTGAGGTCACATGCGTGG
TGGTGGACGTGAGCCACGAAGACCCTGAGGTCAAGTTCAACTGGTACGTG
GACGGCGTGGAGGTGCATAATGCCAAGACAAAGCCGCGGGAGGAGCAGTA
CAACAGCACGTACCGTGTGGTCAGCGTCCTCACCGTCCTGCACCAGGACT
GGCTGAATGGCAAGGAGTACAAGTGCAAGGTCTCCAACAAAGCCCTCCCA
GCCCCCATCGAGAAAACCATCTCCAAAGCCAAAGGGCAGCCCCGAGAACC
ACAGGTGTACACCCTGCCCCCATCCCGGGATGAGCTGACCAAGAACCAGG
TCAGCCTGACCTGCCTGGTCAAAGGCTTCTATCCCAGCGACATCGCCGTG
GAGTGGGAGAGCAATGGGCAGCCGGAGAACAACTACAAGACCACGCCTCC
CGTGCTGGACTCCGACGGCTCCTTCTTCCTCTACAGCAAGCTCACCGTGG
ACAAGAGCAGGTGGCAGCAGGGGAACGTCTTCTCATGCTCCGTGATGCAT
GAGGCTCTGCACAACCACTACACGCAGAAGAGCCTCTCCCTGTCTCCCGG
GAAATGA SEQ ID NO 5:
MSAb-2 heavy chain nucleotide sequence
ATGGGATGGAGCTGTATCATCCTCTTCTTGGTAGCAACAGCTACAGGTGT
ACACAGCCAGGTGCAGCTGGTGCAGTCTGGGGCTGAGGTGAAGAAGCCTG
GGGCCTCAGTGAAGGTTTCCTGCAAGGCATCTGGTTACTCATTCACTGGC
TACACCATGAACTGGGTGCGACAGGCCCCTGGACAAGGGCTTGAGTGGAT
GGGACTTATTACTCCTTACAATGGTGCTTCTAGCTACAACCAGAAGTTCA
GGGGCAGAGTCACCATGACCAGGGACACGTCCACGAGCACAGTCTACATG
GAGCTGAGCAGCCTGAGATCTGAGGACACGGCCGTGTATTACTGTGCGAG
AGGGGGTTACGACGGGAGGGGTTTTGACTACTGGGGATCCGGGACCCCGG
TCACCGTCTCCTCAGCCTCCACCAAGGGCCCATCGGTCTTCCCCCTGGCA
CCCTCCTCCAAGAGCACCTCTGGGGGCACAGCGGCCCTGGGCTGCCTGGT
CAAGGACTACTTCCCCGAACCGGTGACGGTGTCGTGGAACTCAGGCGCCC
TGACCAGCGGCGTGCACACCTTCCCGGCTGTCCTACAGTCCTCAGGACTC
TACTCCCTCAGCAGCGTGGTGACCGTGCCCTCCAGCAGCTTGGGCACCCA
GACCTACATCTGCAACGTGAATCACAAGCCCAGCAACACCAAGGTGGACA
AGAAAGTTGAGCCCAAATCTTGTGACAAAACTCACACATGCCCACCGTGC
CCAGCACCTGAACTCCTGGGGGGACCGTCAGTCTTCCTCTTCCCCCCAAA
ACCCAAGGACACCCTCATGATCTCCCGGACCCCTGAGGTCACATGCGTGG
TGGTGGACGTGAGCCACGAAGACCCTGAGGTCAAGTTCAACTGGTACGTG
GACGGCGTGGAGGTGCATAATGCCAAGACAAAGCCGCGGGAGGAGCAGTA
CAACAGCACGTACCGTGTGGTCAGCGTCCTCACCGTCCTGCACCAGGACT
GGCTGAATGGCAAGGAGTACAAGTGCAAGGTCTCCAACAAAGCCCTCCCA
GCCCCCATCGAGAAAACCATCTCCAAAGCCAAAGGGCAGCCCCGAGAACC
ACAGGTGTACACCCTGCCCCCATCCCGGGATGAGCTGACCAAGAACCAGG
TCAGCCTGACCTGCCTGGTCAAAGGCTTCTATCCCAGCGACATCGCCGTG
GAGTGGGAGAGCAATGGGCAGCCGGAGAACAACTACAAGACCACGCCTCC
CGTGCTGGACTCCGACGGCTCCTTCTTCTTATATTCAAAGCTCACCGTGG
ACAAGAGCAGGTGGCAGCAGGGGAACGTCTTCTCATGCTCCGTGATGCAT
GAGGCTCTGCACAACCACTACACGCAGAAGAGCCTCTCCCTGTCTCCCGG
GAAATGA SEQ ID NO: 9
MSAb-3 heavy chain nucleotide sequence
ATGGGATGGAGCTGTATCATCCTCTTCTTGGTAGCAACAGCTACAGGTGT
ACACAGCCAGGTGCAGCTGGTGCAGTCTGGGGCTGAGGTGAAGAAGCCTG
GGGCCTCAGTGAAGGTTTCCTGCAAGGCATCTGGTTACTCATTCACTGGC
TACACCATGAACTGGGTGAAGCAGGCCCCTGGACAAGGGCTTGAGTGGAT
TGGACTTATTACTCCTTACAATGGTGCTTCTAGCTACAACCAGAAGTTCA
GGGGCAAGGCCACCATGACCAGGGACACGTCCACGAGCACAGTCTACATG
GAGCTGAGCAGCCTGAGATCTGAGGACACGGCCGTGTATTTCTGTGCGAG
AGGGGGTTACGACGGGAGGGGTTTTGACTACTGGGGATCCGGGACCCCGG
TCACCGTCTCCTCAGCCTCCACCAAGGGCCCATCGGTCTTCCCCCTGGCA
CCCTCCTCCAAGAGCACCTCTGGGGGCACAGCGGCCCTGGGCTGCCTGGT
CAAGGACTACTTCCCCGAACCGGTGACGGTGTCGTGGAACTCAGGCGCCC
TGACCAGCGGCGTGCACACCTTCCCGGCTGTCCTACAGTCCTCAGGACTC
TACTCCCTCAGCAGCGTGGTGACCGTGCCCTCCAGCAGCTTGGGCACCCA
GACCTACATCTGCAACGTGAATCACAAGCCCAGCAACACCAAGGTGGACA
AGAAAGTTGAGCCCAAATCTTGTGACAAAACTCACACATGCCCACCGTGC
CCAGCACCTGAACTCCTGGGGGGACCGTCAGTCTTCCTCTTCCCCCCAAA
ACCCAAGGACACCCTCATGATCTCCCGGACCCCTGAGGTCACATGCGTGG
TGGTGGACGTGAGCCACGAAGACCCTGAGGTCAAGTTCAACTGGTACGTG
GACGGCGTGGAGGTGCATAATGCCAAGACAAAGCCGCGGGAGGAGCAGTA
CAACAGCACGTACCGTGTGGTCAGCGTCCTCACCGTCCTGCACCAGGACT
GGCTGAATGGCAAGGAGTACAAGTGCAAGGTCTCCAACAAAGCCCTCCCA
GCCCCCATCGAGAAAACCATCTCCAAAGCCAAAGGGCAGCCCCGAGAACC
ACAGGTGTACACCCTGCCCCCATCCCGGGATGAGCTGACCAAGAACCAGG
TCAGCCTGACCTGCCTGGTCAAAGGCTTCTATCCCAGCGACATCGCCGTG
GAGTGGGAGAGCAATGGGCAGCCGGAGAACAACTACAAGACCACGCCTCC
CGTGCTGGACTCCGACGGCTCCTTCTTCTTATATTCAAAGCTCACCGTGG
ACAAGAGCAGGTGGCAGCAGGGGAACGTCTTCTCATGCTCCGTGATGCAT
GAGGCTCTGCACAACCACTACACGCAGAAGAGCCTCTCCCTGTCTCCCGG
GAAATGA.
```

In some preferred embodiments, the antibodies of the invention comprise a light chain comprising an amino acid sequence of SEQ ID NO:4, SEQ ID NO:8, or SEQ ID NO:12:

```
SEQ ID NO 4:
MSAb-1 light chain amino acid sequence
MGWSCIILFLVATATGVHSDIELTQSPAIMSASPGEKVTMTCSASSSVSY
MHWYQQKSGTSPKRWIYDTSKLASGVPGRFSGSGSGNSYSLTISSVEAED
DATYYCQQWSKHPLTFGSGTKVEIKRTVAAPSVFIFPPSDEQLKSGTASV
VCLLNNFYPREAKVQWKVDNALQSGNSQESVTEQDSKDSTYSLSSTLTLS
KADYEKHKVYACEVTHQGLSSPVTKSFNRGEC*

SEQ ID NO: 8
MSAb-2 light chain amino acid sequence
MGWSCIILFLVATATGVHSEIVLTQSPATLSLSPGERATLSCSASSSVSY
MHWYQQKPGQAPRLLIYDTSKLASGVPARFSGSGSGTDFTLTISSLEPED
FAVYYCQQWSKHPLTFGSGTKVEIKRTVAAPSVFIFPPSDEQLKSGTASV
VCLLNNFYPREAKVQWKVDNALQSGNSQESVTEQDSKDSTYSLSSTLTLS
KADYEKHKVYACEVTHQGLSSPVTKSFNRGEC*

SEQ ID NO: 12
MSAb-3 light chain amino acid sequence
MGWSCIILFLVATATGVHSEIVLTQSPATLSLSPGERATLSCSASSSVSY
MHWYQQKPGQAPRLLIYDTSKLASGVPARFSGSGSGTDFTLTISSLEPED
FAVYYCQQWSKHPLTFGSGTKVEIKRTVAAPSVFIFPPSDEQLKSGTASV
VCLLNNFYPREAKVQWKVDNALQSGNSQESVTEQDSKDSTYSLSSTLTLS
KADYEKHKVYACEVTHQGLSSPVTKSFNRGEC*
```

In some preferred embodiments, the light chain of the antibody is encoded by a nucleotide sequence comprising SEQ ID NO:3, SEQ ID NO:7, or SEQ ID NO:11:

SEQ ID NO 3:
MSAb-1 light chain nucleotide sequence
ATGGGATGGAGCTGTATCATCCTCTTCTTGGTAGCAACAGCTACAGGTGT
ACACTCGGACATCGAGCTCACTCAGTCTCCAGCAATCATGTCTGCATCTC
CAGGGGAGAAGGTCACCATGACCTGCAGTGCCAGCTCAAGTGTAAGTTAC
ATGCACTGGTACCAGCAGAAGTCAGGCACCTCCCCCAAAAGATGGATTTA
TGACACATCCAAACTGGCTTCTGGAGTCCCAGGTCGCTTCAGTGGCAGTG
GGTCTGGGAAACTCTTACTCTCTCACAATCAGCAGCGTGGAGGCTGAAGAT
GATGCAACTTATTACTGCCAGCAGTGGAGTAAGCACCCTCTCACGTTCGG
ATCCGGGACCAAGGTGGAAATCAAACGAACTGTGGCTGCACCATCTGTCT
TCATCTTCCCGCCATCTGATGAGCAGTTGAAATCTGGAACTGCCTCTGTT
GTGTGCCTGCTGAATAACTTCTATCCCAGAGAGGCCAAAGTACAGTGGAA
GGTGGATAACGCCCTCCAATCGGGTAACTCCCAGGAGAGTGTCACAGAGC
AGGACAGCAAGGACAGCACCTACAGCCTCAGCAGCACCCTCTGACGCTGAGC
AAAGCAGACTACGAGAAACACAAAGTCTACGCCTGCGAAGTCACCCATCA
GGGCCTGAGCTCGCCCGTCACAAAGAGCTTCAACAGGGGAGAGTGTTAAT SEQ ID NO: 7
MSAb-2 light chain nucleotide sequence
ATGGGATGGAGCTGTATCATCCTCTTCTTGGTAGCAACAGCTACAGGTGT
ACACAGCGAAATTGTGTTGACACAGTCTCCAGCCACCCTGTCTTTGTCTC
CAGGGGAAAGAGCCACCCTCTCCTGCAGTGCCAGCTCAAGTGTAAGTTAC
ATGCACTGGTACCAACAGAAACCTGGCCAGGCTCCCAGGCTCCTCATCTA
TGACACATCCAAACTGGCTTCTGGCGTCCCAGCCAGGTTCAGTGGCAGTG
GGTCTGGGACAGACTTCACTCTCACCATCAGCAGCCTAGAGCCTGAAGAT
TTTGCAGTTTATTACTGTCAGCAGTGGAGTAAGCACCCTCTCACGTTCGG
ATCCGGGACCAAGGTGGAAATCAAACGAACTGTGGCTGCACCATCTGTCT
TCATCTTCCCGCCATCTGATGAGCAGTTGAAATCTGGAACTGCCTCTGTT
GTGTGCCTGCTGAATAACTTCTATCCCAGAGAGGCCAAAGTACAGTGGAA
GGTGGATAACGCCCTCCAATCGGGTAACTCCCAGGAGAGTGTCACAGAGC
AGGACAGCAAGGACAGCACCTACAGCCTCAGCAGCACCCTCTGACGCTGAGC
AAAGCAGACTACGAGAAACACAAAGTCTACGCCTGCGAAGTCACCCATCA
GGGCCTGAGCTCGCCCGTCACAAAGAGCTTCAACAGGGGAGAGTGTTAA SEQ ID NO: 11
MSAb-3 light chain nucleotide sequence
ATGGGATGGAGCTGTATCATCCTCTTCTTGGTAGCAACAGCTACAGGTGT
ACACAGCGAAATTGTGTTGACACAGTCTCCAGCCACCCTGTCTTTGTCTC
CAGGGGAAAGAGCCACCCTCTCCTGCAGTGCCAGCTCAAGTGTAAGTTAC
ATGCACTGGTACCAACAGAAACCTGGCCAGGCTCCCAGGCTCCTCATCTA
TGACACATCCAAACTGGCTTCTGGCGTCCCAGCCAGGTTCAGTGGCAGTG
GGTCTGGGACAGACTTCACTCTCACCATCAGCAGCCTAGAGCCTGAAGAT
TTTGCAGTTTATTACTGTCAGCAGTGGAGTAAGCACCCTCTCACGTTCGG
ATCCGGGACCAAGGTGGAAATCAAACGAACTGTGGCTGCACCATCTGTCT
TCATCTTCCCGCCATCTGATGAGCAGTTGAAATCTGGAACTGCCTCTGTT
GTGTGCCTGCTGAATAACTTCTATCCCAGAGAGGCCAAAGTACAGTGGAA
GGTGGATAACGCCCTCCAATCGGGTAACTCCCAGGAGAGTGTCACAGAGC
AGGACAGCAAGGACAGCACCTACAGCCTCAGCAGCACCCTCTGACGCTGAGC
AAAGCAGACTACGAGAAACACAAAGTCTACGCCTGCGAAGTCACCCATCA
GGGCCTGAGCTCGCCCGTCACAAAGAGCTTCAACAGGGGAGAGTGTTAA.

In some embodiments of the invention, the antibody comprises a heavy chain comprising an amino acid sequence of SEQ ID NO:2, 6, or 10 and a light chain comprising an amino acid sequence of SEQ ID NO:4, 8, or 12. In more preferred embodiments, the antibody comprises a heavy chain comprising an amino acid sequence of SEQ ID NO:2 and a light chain comprising an amino acid sequence of SEQ ID NO:4; a heavy chain comprising an amino acid sequence of SEQ ID NO:6 and a light chain comprising an amino acid sequence of SEQ ID NO:8; or a heavy chain comprising an amino acid sequence of SEQ ID NO:10 and a light chain comprising an amino acid sequence of SEQ ID NO:12.

The antibodies and derivatives thereof of the invention have binding affinities that include a dissociation constant ($K_d$) of less than $1\times10^{-2}$. In some embodiments, the $K_d$ is less than $1\times10^{-3}$. In other embodiments, the $K_d$ is less than $1\times10^{-4}$. In some embodiments, the $K_d$ is less than $1\times10^{-5}$. In still other embodiments, the $K_d$ is less than $1\times10^{-6}$. In other embodiments, the $K_d$ is less than $1\times10^{-7}$. In other embodiments, the $K_d$ is less than $1\times10^{-8}$. In other embodiments, the $K_d$ is less than $1\times10^{-9}$. In other embodiments, the $K_d$ is less than $1\times10^{-10}$. In still other embodiments, the $K_d$ is less than $1\times10^{-11}$. In some embodiments, the $K_d$ is less than $1\times10^{-12}$. In other embodiments, the $K_d$ is less than $1\times10^{-13}$. In other embodiments, the $K_d$ is less than $1\times10^{-14}$. In still other embodiments, the $K_d$ is less than $1\times10^{-15}$.

The antibodies of the invention may be used alone or with (e.g., coadministered or conjugated to) a biomolecule or chemotherapeutic agent such as a cytotoxic or cytostatic agent. In some embodiments, the chemotherapeutic agent is a radionuclide, including, but not limited to Lead-212, Bismuth-212, Astatine-211, Iodine-131, Scandium-47, Rhenium-186, Rhenium-188, Yttrium-90, Iodine-123, Iodine-125, Bromine-77, Indium-111, and fissionable nuclides such as Boron-10 or an Actinide. In other embodiments, the chemotherapeutic agent is a toxin or cytotoxic drug, including but not limited to ricin, modified *Pseudomonas* enterotoxin A, calicheamicin, adriamycin, 5-fluorouracil, and the like. Methods of conjugation of antibodies and antibody fragments to such agents are known in the literature.

Without wishing to be bound by any particular theory of operation, it is believed that the in-out antibodies of the invention are particularly useful to bind mesothelin due to an increased avidity of the antibody as both "arms" of the antibody (Fab fragments) bind to separate mesothelin molecules. This leads to a decrease in the dissociation (Kd) of the antibody and an overall increase in the observed affinity ($K_D$). In addition, antibodies of this invention bind to epitopes that allow for the internalization of the antibody-antigen complex. These are especially good features for targeting tumors as the antibodies of the invention will bind preferentially to tumor tissue relative to normal tissue to attract immune cells and biomolecules for cytotoxicity and are capable of internalizing for delivery of conjugated agents for therapeutic effect.

Nucleic Acids

The invention also includes nucleic acids encoding the heavy chain and/or light chain of the anti-mesothelin antibodies of the invention. "Nucleic acid" or a "nucleic acid molecule" as used herein refers to any DNA or RNA molecule, either single- or double-stranded and, if single-stranded, the molecule of its complementary sequence in either linear or circular form. In discussing nucleic acid molecules, a sequence or structure of a particular nucleic acid molecule may be described herein according to the normal convention of providing the sequence in the 5' to 3' direction. In some embodiments of the invention, nucleic acids are "isolated." This term, when applied to a nucleic acid molecule, refers to a nucleic acid molecule that is separated from sequences with which it is immediately contiguous in the naturally occurring genome of the organism in which it originated. For example, an "isolated nucleic acid" may comprise a DNA molecule inserted into a vector, such as a plasmid or virus vector, or integrated into the genomic DNA of a prokaryotic or eukaryotic cell or host organism. When applied to RNA, the term "isolated nucleic acid" refers primarily to an RNA molecule encoded by an isolated DNA molecule as defined above. Alternatively, the term may refer to an RNA molecule that has been sufficiently separated from other nucleic acids with which it would be associated in its natural state (i.e., in cells or tissues). An isolated nucleic acid (either DNA or RNA) may further represent a molecule produced directly by biological or synthetic means and separated from other components present during its production.

Nucleic acids of the invention include nucleic acids having at least 80%, more preferably at least about 90%, more preferably at least about 95%, and most preferably at least about 98% homology to nucleic acids of the invention. The terms "percent similarity", "percent identity" and "percent homology" when referring to a particular sequence are used as set forth in the University of Wisconsin GCG software program. Nucleic acids of the invention also include complementary nucleic acids. In some instances, the sequences will be fully complementary (no mismatches) when aligned. In other instances, there may be up to about a 20% mismatch in the sequences.

Nucleic acids of the invention also include fragments of the nucleic acids of the invention. A "fragment" refers to a nucleic acid sequence that is preferably at least about 10 nucleic acids in length, more preferably about 40 nucleic acids, and most preferably about 100 nucleic acids in length. A "fragment" can also mean a stretch of at least about 100 consecutive nucleotides that contains one or more deletions, insertions, or substitutions. A "fragment" can also mean the whole coding sequence of a gene and may include 5' and 3' untranslated regions.

The encoded antibody light chain preferably comprises an amino acid sequence of SEQ ID NO:4, 8, or 12. The encoded antibody heavy chain preferably comprises an amino acid sequence of SEQ ID NO:2, 6, or 10. In some embodiments of the invention, the heavy chain of the antibody is encoded by a nucleic acid comprising the nucleotide sequence of SEQ ID NO:1, 5, or 9. In some embodiments of the invention, the light chain of the anti-mesothelin antibody is encoded by a nucleic acid sequence of SEQ ID NO:3, 7, or 11. In some embodiments of the invention are provided nucleic acids encoding both a heavy chain and a light chain of an antibody of the invention. For example, a nucleic acid of the invention may comprise a nucleic acid sequence encoding an amino acid sequence of SEQ ID NO:2, 6, or 10 and a nucleic acid sequence encoding an amino acid sequence of SEQ ID NO:4, 8, or 12.

Nucleic acids of the invention can be cloned into a vector. A "vector" is a replicon, such as a plasmid, cosmid, bacmid, phage, artificial chromosome (BAC, YAC) or virus, into which another genetic sequence or element (either DNA or RNA) may be inserted so as to bring about the replication of the attached sequence or element. A "replicon" is any genetic element, for example, a plasmid, cosmid, bacmid, phage, artificial chromosome (BAC, YAC) or virus, that is capable of replication largely under its own control. A replicon may be either RNA or DNA and may be single or double stranded. In some embodiments, the expression vector contains a constitutively active promoter segment (such as but not limited to CMV, SV40, Elongation Factor or LTR sequences) or an inducible promoter sequence such as the steroid inducible pIND vector (Invitrogen), where the expression of the nucleic acid can be regulated. Expression vectors of the invention may further comprise regulatory sequences, for example, an internal ribosomal entry site. The expression vector can be introduced into a cell by transfection, for example.

Nucleic acids encoding antibodies of the invention may be recombinantly expressed. The expression cells of the invention include any insect expression cell line known, such as for example, *Spodoptera frugiperda* cells. The expression cell lines may also be yeast cell lines, such as, for example, *Saccharomyces cerevisiae* and *Schizosaccharomyces pombe* cells. The expression cells may also be mammalian cells such as, for example Chinese Hamster Ovary, baby hamster kidney cells, human embryonic kidney line 293, normal dog kidney cell lines, normal cat kidney cell lines, monkey kidney cells, African green monkey kidney cells, COS cells, and non-tumorigenic mouse myoblast G8 cells, fibroblast cell lines, myeloma cell lines, mouse NIH/3T3 cells, LMTK cells, mouse sertoli cells, human cervical carcinoma cells, buffalo rat liver cells, human lung cells, human liver cells, mouse mammary tumor cells, TR1 cells, MRC 5 cells, and FS4 cells. Nucleic acids of the invention may be introduced into a cell by transfection, for example. Recombinantly expressed antibodies may be recovered from the growth medium of the cells, for example.

Methods of Producing in-Out Antibodies to Mesothelin
Immunizing Animals

The invention also provides methods of producing in-out monoclonal antibodies that specifically bind to mesothelin. Antibodies of the invention may be produced in vivo or in vitro. One strategy for generating antibodies against mesothelin involves immunizing animals with mesothelin or cells expressing mesothelin. Animals so immunized will produce antibodies against the protein. Standard methods are known for creating monoclonal antibodies including, but are not limited to, the hybridoma technique (see Kohler & Milstein, (1975) *Nature* 256:495-497); the trioma technique; the human B-cell hybridoma technique (see Kozbor et al. (1983) *Immunol. Today* 4:72) and the EBV hybridoma technique to produce human monoclonal antibodies (see Cole, et al. in MONOCLONAL ANTIBODIES AND CANCER THERAPY, Alan R. Liss, Inc., 1985, pp. 77-96).

For in vivo antibody production, the antigen or antigen-positive cell is generally combined with an adjuvant to promote immunogenicity. Adjuvants vary according to the species used for immunization. Examples of adjuvants include, but are not limited to: Freund's complete adjuvant ("FCA"), Freund's incomplete adjuvant ("FIA"), mineral gels (e.g., aluminum hydroxide), surface active substances (e.g., lysolecithin, pluronic polyols, polyanions), peptides, oil emulsions, keyhole limpet hemocyanin ("KLH"), dinitrophenol ("DNP"), and potentially useful human adjuvants such as Bacille Calmette-Guerin ("BCG") and *corynebacterium parvum*. Such adjuvants are also well known in the art.

Immunization may be accomplished using well-known procedures. The dose and immunization regimen will depend on the species of mammal immunized, its immune status, body weight, and/or calculated surface area, etc. Typically, blood serum is sampled from the immunized mammals and assayed for anti-mesothelin antibodies using appropriate screening assays as described below, for example.

Mesothelin may be purified from cells or from recombinant systems using a variety of well-known techniques for isolating and purifying proteins. For example, but not by way of limitation, mesothelin may be isolated based on the apparent molecular weight of the protein by running the protein on an SDS-PAGE gel and blotting the proteins onto a membrane. Thereafter, the appropriate size band corresponding to mesothelin may be cut from the membrane and used as an immunogen in animals directly, or by first extracting or eluting the protein from the membrane. As an alternative example, the protein may be isolated by size-exclusion chromatography alone or in combination with other means of isolation and purification. Other means of purification are available in such standard reference texts as Zola, MONOCLONAL ANTIBODIES: PREPARATION AND USE OF MONOCLONAL ANTIBODIES AND ENGINEERED ANTIBODY DERIVATIVES (BASICS: FROM BACKGROUND TO BENCH) Springer-Verlag Ltd., New York, 2000; BASIC METHODS IN ANTIBODY PRODUCTION AND CHARACTERIZATION, Chapter 11, "Antibody Purification Methods," Howard and Bethell, Eds., CRC Press, 2000; ANTIBODY ENGINEERING (SPRINGER LAB MANUAL.), Kontermann and Dubel, Eds., Springer-Verlag, 2001.

Another strategy for generating in-out antibodies against mesothelin involves immunizing animals with peptides corresponding to regions of the membrane bound form of mesothelin that allow for internalization of antibodies that retain robust immune effector activity. Animals so immunized will produce antibodies against the protein. Standard methods are known for creating monoclonal antibodies including, but are not limited to, the hybridoma technique (see Kohler & Milstein, (1975) Nature 256:495-497); the trioma technique; the human B-cell hybridoma technique (see Kozbor et al. (1983) Immunol. Today 4:72) and the EBV hybridoma technique to produce human monoclonal antibodies (see Cole, et al. in MONOCLONAL ANTIBODIES AND CANCER THERAPY, Alan R. Liss, Inc., 1985, pp. 77-96).

Splenocytes from immunized animals may be immortalized by fusing the splenocytes (containing the antibody-producing B cells) with an immortal cell line such as a myeloma line. Typically, myeloma cell line is from the same species as the splenocyte donor. In one embodiment, the immortal cell line is sensitive to culture medium containing hypoxanthine, aminopterin and thymidine ("HAT medium"). In some embodiments, the myeloma cells are negative for Epstein-Barr virus (EBV) infection. In preferred embodiments, the myeloma cells are HAT-sensitive, EBV negative and Ig expression negative. Any suitable myeloma may be used. Murine hybridomas may be generated using mouse myeloma cell lines (e.g., the P3-NS1/1-Ag4-1, P3-x63-Ag8.653 or Sp2/O-Ag14 myeloma lines). These murine myeloma lines are available from the ATCC. These myeloma cells are fused to the donor splenocytes polyethylene glycol ("PEG"), preferably 1500 molecular weight polyethylene glycol ("PEG 1500"). Hybridoma cells resulting from the fusion are selected in HAT medium which kills unfused and unproductively fused myeloma cells. Unfused splenocytes die over a short period of time in culture. In some embodiments, the myeloma cells do not express immunoglobulin genes.

Hybridomas producing a desired antibody which are detected by screening assays such as those described below, may be used to produce antibodies in culture or in animals. For example, the hybridoma cells may be cultured in a nutrient medium under conditions and for a time sufficient to allow the hybridoma cells to secrete the monoclonal antibodies into the culture medium. These techniques and culture media are well known by those skilled in the art. Alternatively, the hybridoma cells may be injected into the peritoneum of an unimmunized animal. The cells proliferate in the peritoneal cavity and secrete the antibody, which accumulates as ascites fluid. The ascites fluid may be withdrawn from the peritoneal cavity with a syringe as a rich source of the monoclonal antibody.

Another non-limiting method for producing human antibodies is described in U.S. Pat. No. 5,789,650 which describes transgenic mammals that produce antibodies of another species (e.g., humans) with their own endogenous immunoglobulin genes being inactivated. The genes for the heterologous antibodies are encoded by human immunoglobulin genes. The transgenes containing the unrearranged immunoglobulin encoding regions are introduced into a non-human animal. The resulting transgenic animals are capable of functionally rearranging the transgenic immunoglobulin sequences and producing a repertoire of antibodies of various isotypes encoded by human immunoglobulin genes. The B-cells from the transgenic animals are subsequently immortalized by any of a variety of methods, including fusion with an immortalizing cell line (e.g., a myeloma cell).

In-out antibodies against mesothelin may also be prepared in vitro using a variety of techniques known in the art. For example, but not by way of limitation, fully human monoclonal antibodies against mesothelin may be prepared by using in vitro-primed human splenocytes (Boerner et al. (1991) J. Immunol. 147:86-95).

Alternatively, for example, the antibodies of the invention may be prepared by "repertoire cloning" (Persson et al. (1991) Proc. Nat. Acad. Sci. USA 88:2432-2436; and Huang and Stollar (1991) J. Immunol. Methods 141:227-236). Further, U.S. Pat. No. 5,798,230 describes preparation of human monoclonal antibodies from human B antibody-producing B cells that are immortalized by infection with an Epstein-Barr virus that expresses Epstein-Barr virus nuclear antigen 2 (EBNA2). EBNA2, required for immortalization, is then inactivated resulting in increased antibody titers.

In another embodiment, in-out antibodies against mesothelin are formed by in vitro immunization of peripheral blood mononuclear cells ("PBMCs"). This may be accomplished by any means known in the art, such as, for example, using methods described in the literature (Zafiropoulos et al. (1997) J. Immunological Methods 200:181-190).

In some embodiments of the invention, the procedure for in vitro immunization is supplemented with directed evolution of the hybridoma cells in which a dominant negative allele of a mismatch repair gene such as PMS1, PMS2, PMS2-134, PMSR2, PMSR3, MLH1, MLH2, MLH3, MLH4, MLH5, MLH6, PMSL9, MSH1, and MSH2 is introduced into the hybridoma cells after fusion of the splenocytes, or to the myeloma cells before fusion. Cells containing the dominant negative mutant will become hypermutable and accumulate mutations at a higher rate than untransfected control cells. A pool of the mutating cells may be screened for clones that produce higher affinity antibodies, or that produce higher titers of antibodies, or that simply grow faster or better under certain conditions. The technique for generating hypermutable cells using dominant negative alleles of mismatch repair genes is described in U.S. Pat. No. 6,146,894, issued Nov. 14, 2000. Alternatively, mismatch repair may be inhibited using the chemical inhibitors of mismatch repair described by Nicolaides et al. in WO 02/054856 "Chemical Inhibitors of Mismatch Repair" published Jul. 18, 2002. The technique for enhancing antibodies using the dominant negative alleles of mismatch repair genes or chemical inhibitors of mismatch repair may be applied to mammalian expression cells expressing cloned immunoglobulin genes as well. Cells expressing the dominant negative alleles can be "cured" in that the dominant negative allele can be turned off, if inducible, eliminated from the cell and the like such that the cells become genetically stable once more and no longer accumulate mutations at the abnormally high rate.

Screening for In-Out Antibody Specificity

Screening for in-out antibodies that specifically bind to mesothelin may be accomplished using an enzyme-linked immunosorbent assay (ELISA) in which microtiter plates are coated with immunizing antigen (whole protein or peptides). Antibodies from positively reacting clones can be further screened for reactivity in an ELISA-based assay to mesothelin using microtiter plates coated with mesothelin. Clones that produce antibodies that are reactive to mesothelin are selected for further expansion and development. These antibodies can be further shown for mesothelin specific binding using FACS analysis.

Confirmation of mesothelin reactive in-out antibodies exhibiting may be accomplished, for example, using a standard immune effector assay to monitor antibody dependent cellular cytotoxicity (ADCC). Mesothelin specific antibodies exhibiting ADCC activity can then be conjugated with a fluorochrome or prodrug to monitor ability to internalize by visualization or toxicity that occurs when prodrug is internalized and liberated from the antibody leading to the presence of the toxin.

Pharmaceutical Compositions of Antibodies

Another aspect of the invention features a pharmaceutical composition of anti-mesothelin antibodies of the invention. The pharmaceutical compositions may be used to inhibit or reduce growth of mesothelin-positive cells in vitro or in vivo. For example, the compositions may be administered to a patient to inhibit or reduce growth of tumor cells. In certain embodiments, the pharmaceutical composition is formulated for administration by injection or infusion.

Pharmaceutical compositions of the invention may further comprise one or more chemotherapeutic agents and/or biomolecules. In some embodiments, the antibody is conjugated to the chemotherapeutic agent or biomolecule. Suitable chemotherapeutic agents include but are not limited to a radionuclide, including, but not limited to Lead-212, Bismuth-212, Astatine-211, Iodine-131, Scandium-47, Rhenium-186, Rhenium-188, Yttrium-90, Iodine-123, Iodine-125, Bromine-77, Indium-111, and fissionable nuclides such as Boron-10 or an Actinide. In other embodiments, the agent is a toxin or cytotoxic drug, including but not limited to ricin, modified Pseudomonas enterotoxin A, calicheamicin, adriamycin, 5-fluorouracil, and the like.

Pharmaceutical compositions of the invention may be formulated with a pharmaceutically acceptable carrier or medium. Suitable pharmaceutically acceptable carriers include water, PBS, salt solution (such as Ringer's solution), alcohols, oils, gelatins, and carbohydrates, such as lactose, amylose, or starch, fatty acid esters, hydroxymethylcellulose, and polyvinyl pyrrolidine. Such preparations can be sterilized, and if desired, mixed with auxiliary agents such as lubricants, preservatives, stabilizers, wetting agents, emulsifiers, salts for influencing osmotic pressure, buffers, and coloring. Pharmaceutical carriers suitable for use in the present invention are known in the art and are described, for example, in Pharmaceutical Sciences (17$^{th}$ Ed., Mack Pub. Co., Easton, Pa.).

Kits

According to yet another aspect of the invention, a kit is provided for inhibiting or reducing growth of mesothelin-positive cells, e.g., tumor cells, in vitro or in vivo. Also provided are kits for identifying the presence of mesothelin-positive cells in vitro or in vivo.

The kits of the invention comprise an antibody or an antibody composition of the invention and instructions for using the kit in a method for inhibiting or reducing growth of mesothelin-positive cells or in a method for identifying the presence of mesothelin-positive cells, for example, in a biological sample. The kit may comprise at least one chemotherapeutic reagent. The kit may comprise at least one biomolecule. The kit may comprise at least one diagnostic reagent. An example of a diagnostic reagent is a detectable label, for example but not limited to a radioactive, fluorescent, or chromophoric agent (e.g., $^{111}$In-DOTA). The detectable label may comprise an enzyme. The kit may comprise instructions and/or means for administering the antibody or antibody composition, for example, by injection or infusion.

Methods of Detecting a Mesothelin-Positive Cell

The methods of the invention include methods of detecting mesothelin-positive cells, including but not limited to dysplastic or cancer cells presenting mesothelin on the surface, such as but not limited to ovarian, pancreatic, lung, or mesothelioma cancer cells. The method may be performed in vitro on a biological sample or in vivo. Methods of detecting mesothelin-positive cells according to the invention comprise contacting anti-mesothelin antibody of the invention with a biological sample or administering anti-mesothelin antibody of the invention to a patient, wherein the antibody is labeled with a detectable label, for example but not limited to a radioactive, fluorescent, or chromophoric agent (e.g., $^{111}$In-DOTA), and determining binding of the antibody to cells. Dysplastic or cancer cells associated with increased mesothelin expression will preferably exhibit increased antibody binding relative to normal cells. The detectable label may be an enzyme.

Methods of Reducing the Growth of Mesothelin-Positive Cells

The methods of the invention are suitable for use in humans and non-human animals identified as having mesothelin-positive cells, for example, subjects identified as having a neoplastic condition associated with an increased expression of mesothelin. Non-human animals which benefit from the invention include pets, exotic (e.g., zoo animals) and domestic livestock. Preferably the non-human animals are mammals.

The invention is suitable for use in a human or animal patient that is identified as having a dysplastic disorder that is marked by increased expression of mesothelin in the neoplasm in relation to normal tissues. Once such a patient is identified as in need of treatment for such a condition, the method of the invention may be applied to effect treatment of the condition. Dysplastic tissues that may be treated include, but are not limited to ovary, lung, pancreas, and prostate.

The in-out antibodies and derivatives thereof for use in the invention may be administered orally in any acceptable dosage form such as capsules, tablets, aqueous suspensions, solutions or the like. The antibodies and derivatives thereof may also be administered parenterally, for example, via the following routes of administration: subcutaneous, intravenous, intramuscular, intra-articular, intra-synovial, intrasternal, intranasal, topically, intrathecal, intrahepatic, intralesional, and intracranial injection or infusion techniques. Generally, the antibodies and derivatives will be provided as an intramuscular or intravenous injection.

The in-out antibodies and derivatives of the invention may be administered alone or with a pharmaceutically acceptable carrier, including acceptable adjuvants, vehicles and excipients, for example, phosphate buffered saline The effective dosage will depend on a variety of factors and it is well within the purview of a skilled physician to adjust the dosage for a given patient according to various parameters such as body weight, the goal of treatment, the highest tolerated dose, the specific formulation used, the route of administration and the like. Generally, dosage levels of between about 0.001 and about 100 mg/kg body weight per day of the antibody or derivative thereof are suitable. In some embodiments, the dose will be about 0.1 to about 50 mg/kg body weight per day of the antibody or derivative thereof. In other embodiments, the dose will be about 0.1 mg/kg body weight/day to about 20 mg/kg body weight/day. In still other embodiments, the dose will be about 0.1 mg/kg body weight/day to about 10 mg/kg body weight/day. Dosing may be as a bolus or an infusion. Dosages may be given once a day or multiple times in a day. Further, dosages may be given multiple times of a period of time. In some embodiments, the doses are given every 1-14 days. In some embodiments, the antibodies or derivatives thereof are given as a dose of about. 3 to 1 mg/kg i.p. In other embodiments, the antibodies of derivatives thereof are provided at about 5 to 12.5 mg/kg i.v. In still other embodiments, the antibodies or derivatives thereof are provided such that a plasma level of at least about 1 ug/ml is maintained.

Effective treatment may be assessed in a variety of ways. In one embodiment, effective treatment is determined by a slowed progression of tumor growth. In other embodiments, effective treatment is marked by shrinkage of the tumor (i.e., decrease in the size of the tumor). In other embodiments, effective treatment is marked by inhibition of metastasis of the tumor. In still other embodiments, effective therapy is measured by increased well-being of the patient including such signs as weight gain, regained strength, decreased pain, thriving, and subjective indications from the patient of better health.

The antibodies of the invention may be administered before, after, or simultaneously with another therapeutic or diagnostic agent. For example, the in-out antibodies of the invention may be administered alone or with a cytotoxic agent such as but not limited to adriamycin, doxorubicin, gemcitabine, or 5-fluorouracil. The in-out antibodies of the invention may be administered alone or with a cytostatic agent such as but not limited to tarceva and avastin. The in-out antibodies and derivatives of the invention may be administered alone or with a vaccine agent. The in-out antibodies and derivatives of the invention may be administered alone or with another biomolecule such as but not limited to interleukin-2, interferon alpha, interferon beta, interferon gamma, rituxan, zevalin, herceptin, erbitux, avastin.

The in-out antibodies and derivatives of the invention may be administered as a homogeneous mixture of unconjugated or conjugated antibody or as a heterogeneous mixture of unconjugated and conjugated in-out antibody.

The following Examples are provided to illustrate the present invention, and should not be construed as limiting thereof.

EXAMPLES

Example 1

In-Out Antibodies that can Bind to Mesothelin

The monoclonal antibody MSAb-1 was developed by cloning the variable domain of a mesothelin FAb fragment to the human IgG1 constant region. The antibody was shown to bind specifically to mesothelin protein and cancer cells expressing mesothelin and was found to have a binding constant of 2 nM using BIACORE. MSAb-2 and MSAb-3 are variants of MSAb-1 that have different nucleotide and amino acid sequences within their respective variable regions. To demonstrate mesothelin-specific binding, ELISA assays were performed using recombinant mesothelin in a 96-well format following methods used by those skilled in the art. Antibodies found to react by ELISA were further analyzed for mesothelin binding using FACS analysis following the manufacturer's protocol. Shown in FIG. 1 are representative data of the FACS analysis whereby mesothelin-expressing ovarian and pancreatic tumor cells were positive for MSAb-1 binding in contrast to null cells (A549).

Example 2

Immune Effector Activity of MSAB-1

Activity of MSAb-1 In-out antibody for immune effector activity was assessed by standard antibody dependent cellular cytotoxicity (ADCC) assays on the mesothelin expressing OVCAR-3 cell line. Briefly, OVCAR-3 target cells were seeded in flat-bottom 96-well microplates in complete growth medium (RPMI-1640 containing 10% FBS, 2 mM L-glutamine). The following day, the complete medium was replaced with 100 µl of CHO-CD serum-free medium (Sigma) and 50 µl of antibody-containing conditioned medium was added to target cells and incubated for 20 minutes at 37° C. Subsequently, 100 µl of serum-free medium containing $2 \times 10^5$ of effector cells were added to each well and cells were incubated for 5-6 hours at 37° C., 5% $CO_2$. Effector cells were derived from human peripheral blood mononuclear cells (PBMCs) isolated from healthy donors (purchased from Interstate Blood Bank). Prior to use in ADCC assays, PBMCs were activated by seeding PBMCs at $2.5 \times 10^6$/ml in complete RPMI containing 10 ng/ml human recombinant interleukin 2 (R&D Systems) for 3 days at 37° C., 5% $CO_2$. Activated PBMCs were then added to OVCAR-3 cells at an effector: target cell ratio of 5:1 and cultures were incubated for 5-6 hours at 37° C., 5% $CO_2$. Supernatant was then collected from each well and transferred into ELISA plates and analyzed for ADCC activity as follows. ADCC activity was monitored by lactate dehydrogenase (LDH) release, an endogenous enzyme used to measure ADCC in standard assays. LDH was monitored by adding 100 µl of LDH substrate (Roche), a chemical that when converted by LDH is spectrophotometrically detectable at $OD_{490}$, to supernatant and incubated for 10 minutes at ambient temperature. LDH activity is proportional to the extent of the LDH enzyme released from lysed target cells. Optical density at 490 nm ($OD_{490}$) was obtained spectrophotometrically. 2% Triton X was added to target cells alone as a "max" positive control, while target cells with PBMC and no antibody served as the "spontaneous" negative control. LDH values were obtained and percent of cytotoxicity was determined with the formula: (sample value−spontaneous)/(max−spontaneous)×100%, where 'spontaneous'=target cell lysis in absence of effector cells, and 'max'=target cell lysis in the presence of 2% Triton. Cytotoxicity elicited by 100 ng/ml of MORAb-A92 (protein A purified), an isotype control antibody, was used as positive control. Non-specific cytotoxicity was monitored using 100 ng/ml of normal human IgG1 antibody. The ratio obtained dividing the % cytotoxicity by the concentration of the antibody for each well/clone (i.e. ratio=50(%)/100(ng/ml)=0.5) was set as the criterion for selecting lead clones with potentially enhanced effector function.

Figure 2:
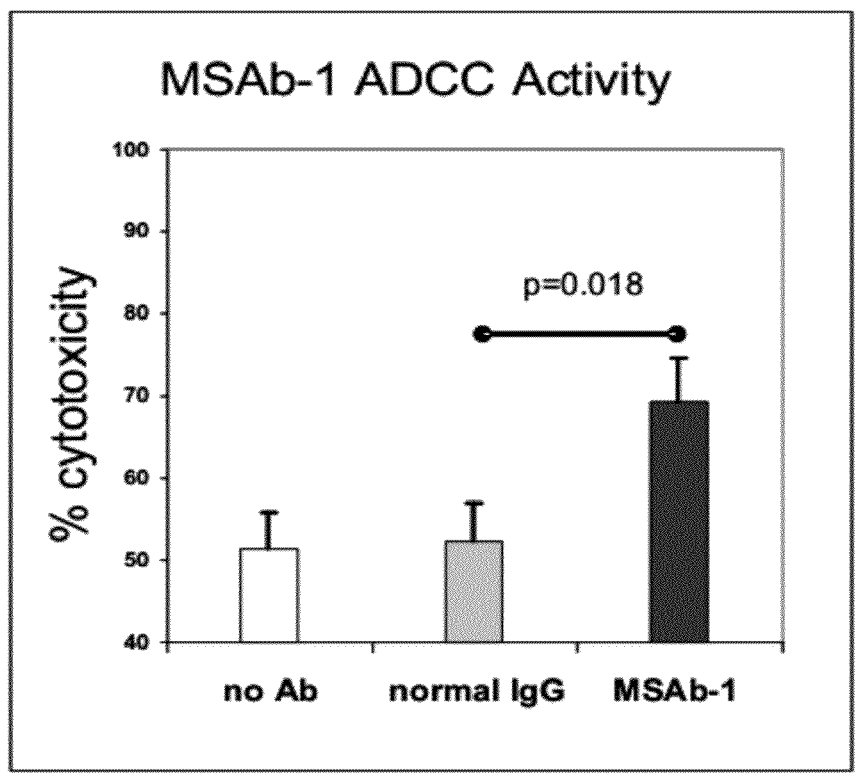
FIG. 2 demonstrates that MSAb-1 elicits a robust antibody dependent cellular cytotoxicity (ADCC) activity. Tumor cell line OVCAR-3 (referred to as target) which expresses mesothelin was incubated with human peripheral blood lymphocytes (PBLs) alone (no Ab lane); with MSAb-1 and PBLs; or with control Ig and PBLs (normal IgG). Cell cultures were assayed for killing by monitoring for lactate dehydrogenase (LDH) release that occurs upon cell lysis. As shown here, MSAb-1 has ADCC activity on mesothelin-expressing cells.

Analysis of MSAb-1 shows the ability to enhance ADCC activity (p=0.018) over cells incubated with control Ig or no antibody (FIG. 2). These data support the finding that MSAb-1 has cytotoxic effects via immune effector function.

Example 3

Internalization of MSAb-1

Figure 3:
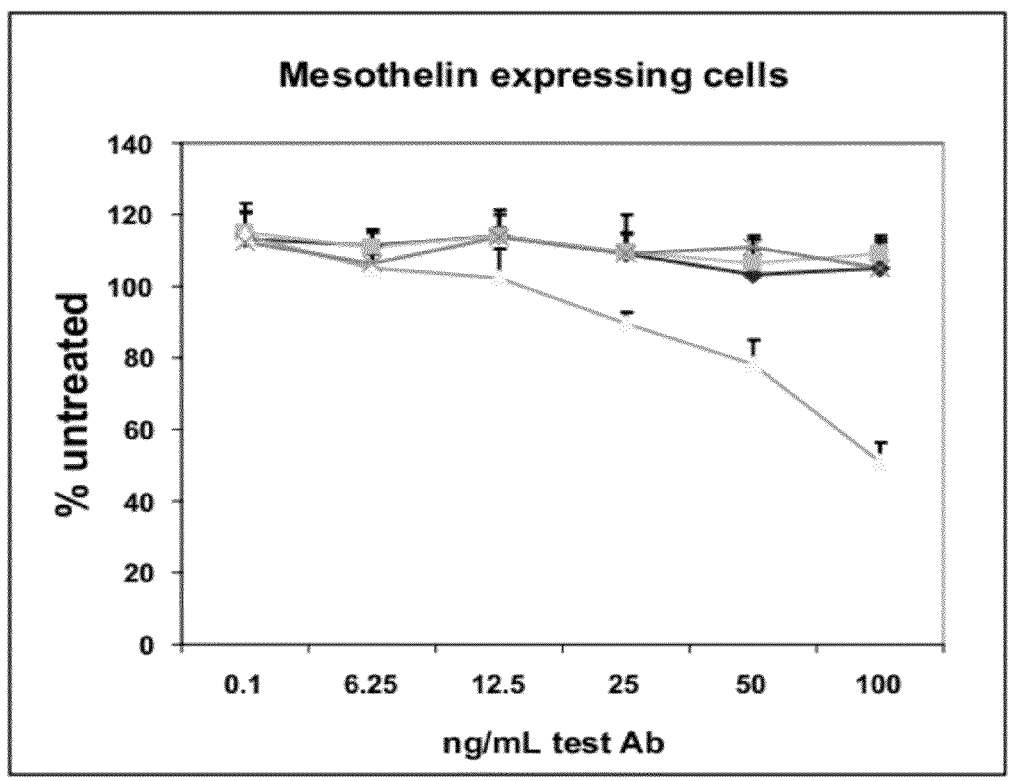
FIG. 3 demonstrates that MSAb-1 internalizes in mesothelin-expressing cells.

MSAb-1 internalizes when bound to mesothelin-expressing cells. This finding is shown in FIG. 3 using the Hum-ZAP assay. Second immunotoxins are conjugations of a secondary antibody to the ribosome inactivating protein saporin. If the primary antibody being tested is internalized, the saporin is transported into the cell via its binding to the secondary antibody. Once internalized, saporin separates from its IgG conjugate, inhibits protein synthesis, and ultimately causes cell death. Hum-ZAP (Advanced Targeting Systems, cat#IT-22) is a secondary chemical conjugate of affinity purified goat anti-human IgG, (mw 210 kDa) that recognizes human monoclonal antibodies. The control molecule, Goat IgG-SAP (Advanced Targeting Systems cat#IT-19) is a conjugate of normal goat IgG and saporin. Briefly, cells were plated into flat-bottom 96-well tissue culture plates at 2500/well in 80 µl of RPMI 1640 with 10% FCS, 2.0 mM glutamine, 1.0 mM sodium pyruvate, and 0.1 mM MEM non-essential amino acids. Twenty-four hours later, 10 µl of primary antibodies ML-1 or MSAb-1 were added along with 10 µl of Hum-ZAP or Goat IgG-SAP to bring the total volume to 100 μl. Experiments were set up with antibody titrations and include primary and secondary antibodies alone as control. Four days later, cell viability was evaluated using Promega CellTiter® Cytotoxicity Assay (cat#G3581) which reads viable cell number by spectrophotometry. All tests were performed in triplicate. Data was evaluated by comparing treated and untreated wells and results are expressed as percent of control. As shown in FIG. 3, OVCAR-3 cells, which overexpress mesothelin (triangle) die upon treatment with toxin-conjugated MSAb-1 as compared to toxin-conjugated and unconjugated isotype control ML1 antibody (diamond and square, respectively) and to unconjugated MSAb-1 (X). In contrast, MSAb-1 toxin conjugate has no cytotoxicity on mesothelin-null TP cells as compared to positive control ML1 conjugated antibody which recognizes a cell surface antigen expressed on TP cells.

SUMMARY

In summary, anti-mesothelin antibodies of the invention are capable of eliciting ADCC yet internalize in mesothelin-positive cells. The antibodies of the invention are useful for the treatment of mesothelin-positive tumor cells either as a single agent or in combination therapy.

The invention claimed is:

1. A pharmaceutical composition comprising a pharmaceutically acceptable carrier and an antibody that specifically binds to mesothelin and is capable of both eliciting an immune effector activity and internalizing within mesothelin-positive cells, the antibody comprising a heavy chain variable domain comprising the amino acid sequence of SEQ ID NO: 2 absent amino acids 1 to 19 thereof and a light chain variable domain comprising the amino acid sequence of SEQ ID NO: 4 absent amino acids 1 to 19 thereof; a heavy chain variable domain comprising the amino acid sequence of SEQ ID NO: 6 absent amino acids 1 to 19 thereof and a light chain variable domain comprising the amino acid sequence of SEQ ID NO: 8 absent amino acids 1 to 19 thereof; or a heavy chain variable domain comprising the amino acid sequence of SEQ ID NO: 10 absent amino acids 1 to 19 thereof and a light chain variable domain comprising the amino acid sequence of SEQ ID NO: 12 absent amino acids 1 to 19 thereof.

2. The pharmaceutical composition of claim 1 comprising a chemotherapeutic agent.

3. The pharmaceutical composition of claim 1 comprising a biomolecule.

* * * * *

SEQUENCE LISTING

<160> NUMBER OF SEQ ID NOS: 12

<210> SEQ ID NO 1
<211> LENGTH: 1407
<212> TYPE: DNA
<213> ORGANISM: Artificial Sequence
<220> FEATURE:
<223> OTHER INFORMATION: Oligonucleotide

<400> SEQUENCE: 1

```
atgggatgga gctgtatcat cctcttcttg gtagcaacag ctacaggtgt acacagccag    60
gtacaactgc agcagtctgg gcctgagctg gagaagcctg gcgcttcagt gaagatatcc   120
tgcaaggctt ctggttactc attcactggc tacaccatga actgggtgaa gcagagccat   180
ggaaagagcc ttgagtggat tggacttatt actccttaca atggtgcttc tagctacaac   240
cagaagttca ggggcaaggc cacattaact gtagacaagt catccagcac agcctacatg   300
gacctcctca gtctgacatc tgaagactct gcagtctatt tctgtgcaag gggggggttac   360 gacgggaggg gttttgacta ctggggatcc gggacccecgg tcaccgtctc ctcagcctcc   420
accaagggcc catcggtctt ccccctggca ccctcctcca agagcacctc tgggggcaca   480
gcggccctgg gctgcctggt caaggactac ttccccgaac cggtgacggt gtcgtggaac   540
tcaggcgccc tgaccagcgg cgtgcacacc ttcccggctg tcctacagtc ctcaggactc   600
tactccctca gcagcgtggt gaccgtgccc tccagcagct gggcaccca gacctacatc   660 tgcaacgtga atcacaagcc cagcaacacc aaggtggaca gaaagttga gcccaaatct   720 tgtgacaaaa ctcacacatg cccaccgtgc ccagcacctg aactcctggg gggaccgtca   780
gtcttcctct tccccccaaa acccaaggac accctcatga tctcccggac ccctgaggtc   840
acatgcgtgg tggtggacgt gagccacgaa gaccctgagg tcaagttcaa ctggtacgtg   900
gacggcgtgg aggtgcataa tgccaagaca aagccgcggg aggagcagta caacagcacg   960
taccgtgtgg tcagcgtcct caccgtcctg caccaggact ggctgaatgg caaggagtac  1020
aagtgcaagg tctccaacaa agccctccca gcccccatcg agaaaaccat ctccaaagcc  1080
aaagggcagc cccgagaacc acaggtgtac accctgcccc catcccggga tgagctgacc  1140
aagaaccagg tcagcctgac ctgcctggtc aaaggcttct atcccagcga catcgccgtg  1200
gagtgggaga gcaatgggca gccggagaac aactacaaga ccacgcctcc cgtgctggac  1260
tccgacggct ccttcttcct ctacagcaag ctcaccgtgg acaagagcag gtggcagcag  1320
gggaacgtct tctcatgctc cgtgatgcat gaggctctgc acaaccacta cacgcagaag  1380
agcctctccc tgtctcccgg gaaatga                                     1407
```

<210> SEQ ID NO 2
<211> LENGTH: 468
<212> TYPE: PRT
<213> ORGANISM: Artificial Sequence
<220> FEATURE:
<223> OTHER INFORMATION: Synthetic Construct

<400> SEQUENCE: 2

```
Met Gly Trp Ser Cys Ile Ile Leu Phe Leu Val Ala Thr Ala Thr Gly
1               5                   10                  15

Val His Ser Gln Val Gln Leu Gln Gln Ser Gly Pro Glu Leu Glu Lys
            20                  25                  30

Pro Gly Ala Ser Val Lys Ile Ser Cys Lys Ala Ser Gly Tyr Ser Phe
        35                  40                  45

Thr Gly Tyr Thr Met Asn Trp Val Lys Gln Ser His Gly Lys Ser Leu
    50                  55                  60

Glu Trp Ile Gly Leu Ile Thr Pro Tyr Asn Gly Ala Ser Ser Tyr Asn
65                  70                  75                  80

Gln Lys Phe Arg Gly Lys Ala Thr Leu Thr Val Asp Lys Ser Ser Ser
                85                  90                  95

Thr Ala Tyr Met Asp Leu Leu Ser Leu Thr Ser Glu Asp Ser Ala Val
            100                 105                 110

Tyr Phe Cys Ala Arg Gly Gly Tyr Asp Gly Arg Gly Phe Asp Tyr Trp
        115                 120                 125

Gly Ser Gly Thr Pro Val Thr Val Ser Ser Ala Ser Thr Lys Gly Pro
    130                 135                 140

Ser Val Phe Pro Leu Ala Pro Ser Ser Lys Ser Thr Ser Gly Gly Thr
145                 150                 155                 160

Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
            180                 185                 190

Ala Val Leu Gln Ser Ser Gly Leu Tyr Ser Leu Ser Ser Val Val Thr
        195                 200                 205

Val Pro Ser Ser Ser Leu Gly Thr Gln Thr Tyr Ile Cys Asn Val Asn
    210                 215                 220

His Lys Pro Ser Asn Thr Lys Val Asp Lys Lys Val Glu Pro Lys Ser
225                 230                 235                 240

Cys Asp Lys Thr His Thr Cys Pro Pro Cys Pro Ala Pro Glu Leu Leu
                245                 250                 255

Gly Gly Pro Ser Val Phe Leu Phe Pro Pro Lys Pro Lys Asp Thr Leu
            260                 265                 270

Met Ile Ser Arg Thr Pro Glu Val Thr Cys Val Val Val Asp Val Ser
        275                 280                 285

His Glu Asp Pro Glu Val Lys Phe Asn Trp Tyr Val Asp Gly Val Glu
    290                 295                 300

Val His Asn Ala Lys Thr Lys Pro Arg Glu Glu Gln Tyr Asn Ser Thr
305                 310                 315                 320

Tyr Arg Val Val Ser Val Leu Thr Val Leu His Gln Asp Trp Leu Asn
                325                 330                 335

Gly Lys Glu Tyr Lys Cys Lys Val Ser Asn Lys Ala Leu Pro Ala Pro
            340                 345                 350

Ile Glu Lys Thr Ile Ser Lys Ala Lys Gly Gln Pro Arg Glu Pro Gln
        355                 360                 365

Val Tyr Thr Leu Pro Pro Ser Arg Asp Glu Leu Thr Lys Asn Gln Val
    370                 375                 380
```

Ser Leu Thr Cys Leu Val Lys Gly Phe Tyr Pro Ser Asp Ile Ala Val
385                 390                 395                 400

Glu Trp Glu Ser Asn Gly Gln Pro Glu Asn Asn Tyr Lys Thr Thr Pro
            405                 410                 415

Pro Val Leu Asp Ser Asp Gly Ser Phe Phe Leu Tyr Ser Lys Leu Thr
            420                 425                 430

Val Asp Lys Ser Arg Trp Gln Gln Gly Asn Val Phe Ser Cys Ser Val
            435                 440                 445

Met His Glu Ala Leu His Asn His Tyr Thr Gln Lys Ser Leu Ser Leu
    450                 455                 460

Ser Pro Gly Lys
465

<210> SEQ ID NO 3
<211> LENGTH: 700
<212> TYPE: DNA
<213> ORGANISM: Artificial Sequence
<220> FEATURE:
<223> OTHER INFORMATION: Oligonucleotide

<400> SEQUENCE: 3
atgggatgga gctgtatcat cctcttcttg gtagcaacag ctacaggtgt acactcggac      60
atcgagctca ctcagtctcc agcaatcatg tctgcatctc caggggagaa ggtcaccatg     120
acctgcagtg ccagctcaag tgtaagttac atgcactggt accagcagaa gtcaggcacc     180
tcccccaaaa gatggattta tgacacatcc aaactggctt ctggagtccc aggtcgcttc     240
agtggcagtg ggtctgggaa actcttactct ctcacaatca gcagcgtgga ggctgaagat     300
gatgcaactt attactgcca gcagtggagt aagcaccctc tcacgttcgg atccgggacc     360
aaggtggaaa tcaaacgaac tgtggctgca ccatctgtct tcatcttccc gccatctgat     420
gagcagttga aatctggaac tgcctctgtt gtgtgcctgc tgaataactt ctatcccaga     480
gaggccaaag tacagtggaa ggtggataac gccctccaat cgggtaactc ccaggagagt     540
gtcacagagc aggacagcaa ggacagcacc tacagcctca gcagcaccct gacgctgagc     600
aaagcagact acgagaaaca caaagtctac gcctgcgaag tcacccatca gggcctgagc     660
tcgcccgtca caaagagctt caacagggga gagtgttaat                            700

<210> SEQ ID NO 4
<211> LENGTH: 232
<212> TYPE: PRT
<213> ORGANISM: Artificial Sequence
<220> FEATURE:
<223> OTHER INFORMATION: Synthetic Construct

<400> SEQUENCE: 4

Met Gly Trp Ser Cys Ile Ile Leu Phe Leu Val Ala Thr Ala Thr Gly
1               5                   10                  15

Val His Ser Asp Ile Glu Leu Thr Gln Ser Pro Ala Ile Met Ser Ala
            20                  25                  30

Ser Pro Gly Glu Lys Val Thr Met Thr Cys Ser Ala Ser Ser Ser Val
        35                  40                  45

Ser Tyr Met His Trp Tyr Gln Gln Lys Ser Gly Thr Ser Pro Lys Arg
    50                  55                  60

Trp Ile Tyr Asp Thr Ser Lys Leu Ala Ser Gly Val Pro Gly Arg Phe
65                  70                  75                  80

Ser Gly Ser Gly Ser Gly Asn Ser Tyr Ser Leu Thr Ile Ser Ser Val
                85                  90                  95

Glu Ala Glu Asp Asp Ala Thr Tyr Tyr Cys Gln Gln Trp Ser Lys His
            100                 105                 110

Pro Leu Thr Phe Gly Ser Gly Thr Lys Val Glu Ile Lys Arg Thr Val
        115                 120                 125

Ala Ala Pro Ser Val Phe Ile Phe Pro Pro Ser Asp Glu Gln Leu Lys
    130                 135                 140

Ser Gly Thr Ala Ser Val Val Cys Leu Leu Asn Asn Phe Tyr Pro Arg
145                 150                 155                 160

Glu Ala Lys Val Gln Trp Lys Val Asp Asn Ala Leu Gln Ser Gly Asn
                165                 170                 175

Ser Gln Glu Ser Val Thr Glu Gln Asp Ser Lys Asp Ser Thr Tyr Ser
            180                 185                 190

Leu Ser Ser Thr Leu Thr Leu Ser Lys Ala Asp Tyr Glu Lys His Lys
        195                 200                 205

Val Tyr Ala Cys Glu Val Thr His Gln Gly Leu Ser Ser Pro Val Thr
    210                 215                 220

Lys Ser Phe Asn Arg Gly Glu Cys
225                 230

<210> SEQ ID NO 5
<211> LENGTH: 1407
<212> TYPE: DNA
<213> ORGANISM: Artificial Sequence
<220> FEATURE:
<223> OTHER INFORMATION: Olligonucleotide

<400> SEQUENCE: 5

```
atgggatgga gctgtatcat cctcttcttg gtagcaacag ctacaggtgt acacagccag     60
gtgcagctgg tgcagtctgg ggctgaggtg aagaagcctg ggcctcagt gaaggtttcc    120
tgcaaggcat ctggttactc attcactggc tacaccatga actgggtgcg acaggcccct    180
ggacaagggc ttgagtggat gggacttatt actccttaca tggtgcttc tagctacaac    240
cagaagttca gggcagagt caccatgacc agggacacgt ccacgagcac agtctacatg    300
gagctgagca gcctgagatc tgaggacacg gccgtgtatt actgtgcgag aggggggttac    360
gacgggaggg ttttgactac tggggatcc gggaccccgg tcaccgtctc ctcagcctcc    420
accaagggcc catcggtctt ccccctggca ccctcctcca agagcacctc tgggggcaca    480
gcggccctgg gctgcctggt caaggactac ttccccgaac cggtgacggt gtcgtggaac    540
tcaggcgccc tgaccagcgg cgtgcacacc ttcccggctg tcctacagtc ctcaggactc    600
tactccctca gcagcgtggt gaccgtgccc tccagcagct gggcaccca gacctacatc    660
tgcaacgtga atcacaagcc cagcaacacc aaggtggaca gaaagttga gcccaaatct    720
tgtgacaaaa ctcacacatg cccaccgtgc ccagcacctg aactcctggg gggaccgtca    780
gtcttcctct tccccccaaa acccaaggac accctcatga tctcccggac ccctgaggtc    840
acatgcgtgg tggtggacgt gagccacgaa gaccctgagg tcaagttcaa ctggtacgtg    900
gacggcgtgg aggtgcataa tgccaagaca aagccgcggg aggagcagta caacagcacg    960
taccgtgtgg tcagcgtcct caccgtcctg caccaggact ggctgaatgg caaggagtac   1020
aagtgcaagg tctccaacaa agccctccca gcccccatcg agaaaaccat ctccaaagcc   1080
aaagggcagc cccgagaacc acaggtgtac accctgcccc catcccggga tgagctgacc   1140
aagaaccagg tcagcctgac ctgcctggtc aaaggcttct atcccagcga catcgccgtg   1200
gagtgggaga gcaatgggca gccggagaac aactacaaga ccacgcctcc cgtgctggac   1260
```

```
tccgacggct ccttcttctt atattcaaag ctcaccgtgg acaagagcag gtggcagcag    1320
gggaacgtct tctcatgctc cgtgatgcat gaggctctgc acaaccacta cacgcagaag    1380
agcctctccc tgtctcccgg gaaatga                                        1407
```

<210> SEQ ID NO 6
<211> LENGTH: 468
<212> TYPE: PRT
<213> ORGANISM: Artificial Sequence
<220> FEATURE:
<223> OTHER INFORMATION: Synthetic Construct

<400> SEQUENCE: 6

```
Met Gly Trp Ser Cys Ile Ile Leu Phe Leu Val Ala Thr Ala Thr Gly
1               5                   10                  15

Val His Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Ser Phe
        35                  40                  45

Thr Gly Tyr Thr Met Asn Trp Val Arg Gln Ala Pro Gly Gln Gly Leu
    50                  55                  60

Glu Trp Met Gly Leu Ile Thr Pro Tyr Asn Gly Ala Ser Ser Tyr Asn
65                  70                  75                  80

Gln Lys Phe Arg Gly Arg Val Thr Met Thr Arg Asp Thr Ser Thr Ser
                85                  90                  95

Thr Val Tyr Met Glu Leu Ser Ser Leu Arg Ser Glu Asp Thr Ala Val
            100                 105                 110

Tyr Tyr Cys Ala Arg Gly Gly Tyr Asp Gly Arg Gly Phe Asp Tyr Trp
        115                 120                 125

Gly Ser Gly Thr Pro Val Thr Val Ser Ser Ala Ser Thr Lys Gly Pro
    130                 135                 140

Ser Val Phe Pro Leu Ala Pro Ser Ser Lys Ser Thr Ser Gly Gly Thr
145                 150                 155                 160

Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
            180                 185                 190

Ala Val Leu Gln Ser Ser Gly Leu Tyr Ser Leu Ser Ser Val Val Thr
        195                 200                 205

Val Pro Ser Ser Ser Leu Gly Thr Gln Thr Tyr Ile Cys Asn Val Asn
    210                 215                 220

His Lys Pro Ser Asn Thr Lys Val Asp Lys Lys Val Glu Pro Lys Ser
225                 230                 235                 240

Cys Asp Lys Thr His Thr Cys Pro Pro Cys Pro Ala Pro Glu Leu Leu
                245                 250                 255

Gly Gly Pro Ser Val Phe Leu Phe Pro Pro Lys Pro Lys Asp Thr Leu
            260                 265                 270

Met Ile Ser Arg Thr Pro Glu Val Thr Cys Val Val Val Asp Val Ser
        275                 280                 285

His Glu Asp Pro Glu Val Lys Phe Asn Trp Tyr Val Asp Gly Val Glu
    290                 295                 300

Val His Asn Ala Lys Thr Lys Pro Arg Glu Glu Gln Tyr Asn Ser Thr
305                 310                 315                 320

Tyr Arg Val Val Ser Val Leu Thr Val Leu His Gln Asp Trp Leu Asn
                325                 330                 335

Gly Lys Glu Tyr Lys Cys Lys Val Ser Asn Lys Ala Leu Pro Ala Pro
```

```
            340             345             350
Ile Glu Lys Thr Ile Ser Lys Ala Lys Gly Gln Pro Arg Glu Pro Gln
            355             360             365

Val Tyr Thr Leu Pro Pro Ser Arg Asp Glu Leu Thr Lys Asn Gln Val
        370             375             380

Ser Leu Thr Cys Leu Val Lys Gly Phe Tyr Pro Ser Asp Ile Ala Val
385             390             395             400

Glu Trp Glu Ser Asn Gly Gln Pro Glu Asn Asn Tyr Lys Thr Thr Pro
                405             410             415

Pro Val Leu Asp Ser Asp Gly Ser Phe Phe Leu Tyr Ser Lys Leu Thr
            420             425             430

Val Asp Lys Ser Arg Trp Gln Gln Gly Asn Val Phe Ser Cys Ser Val
        435             440             445

Met His Glu Ala Leu His Asn His Tyr Thr Gln Lys Ser Leu Ser Leu
    450             455             460

Ser Pro Gly Lys
465

<210> SEQ ID NO 7
<211> LENGTH: 699
<212> TYPE: DNA
<213> ORGANISM: Artificial Sequence
<220> FEATURE:
<223> OTHER INFORMATION: Oligonucleotide

<400> SEQUENCE: 7
atgggatgga gctgtatcat cctcttcttg gtagcaacag ctacaggtgt acacagcgaa      60
attgtgttga cacagtctcc agccaccctg tctttgtctc caggggaaag agccacccct     120
tcctgcagtg ccagctcaag tgtaagttac atgcactggt accaacagaa acctggccag     180
gctcccaggc tcctcatcta tgacacatcc aaactggctt ctggcgtccc agccaggttc     240
agtggcagtg ggtctgggac agacttcact ctcaccatca gcagcctaga gcctgaagat     300
tttgcagttt attactgtca gcagtggagt aagcaccctc tcacgttcgg atccgggacc     360
aaggtggaaa tcaaacgaac tgtggctgca ccatctgtct tcatcttccc gccatctgat     420
gagcagttga aatctggaac tgcctctgtt gtgtgcctgc tgaataactt ctatcccaga     480
gaggccaaag tacagtggaa ggtggataac gccctccaat cgggtaactc ccaggagagt     540
gtcacagagc aggacagcaa ggacagcacc tacagcctca gcagcaccct gacgctgagc     600
aaagcagact acgagaaaca caaagtctac gcctgcgaag tcacccatca gggcctgagc     660
tcgcccgtca caaagagctt caacagggga gagtgttaa                            699

<210> SEQ ID NO 8
<211> LENGTH: 232
<212> TYPE: PRT
<213> ORGANISM: Artificial Sequence
<220> FEATURE:
<223> OTHER INFORMATION: Synthetic Construct

<400> SEQUENCE: 8

Met Gly Trp Ser Cys Ile Ile Leu Phe Leu Val Ala Thr Ala Thr Gly
1               5                   10                  15

Val His Ser Glu Ile Val Leu Thr Gln Ser Pro Ala Thr Leu Ser Leu
            20                  25                  30

Ser Pro Gly Glu Arg Ala Thr Leu Ser Cys Ser Ala Ser Ser Ser Val
        35                  40                  45

Ser Tyr Met His Trp Tyr Gln Gln Lys Pro Gly Gln Ala Pro Arg Leu
```

```
                50                  55                  60
Leu Ile Tyr Asp Thr Ser Lys Leu Ala Ser Gly Val Pro Ala Arg Phe
 65                  70                  75                  80

Ser Gly Ser Gly Ser Gly Thr Asp Phe Thr Leu Thr Ile Ser Ser Leu
                 85                  90                  95

Glu Pro Glu Asp Phe Ala Val Tyr Tyr Cys Gln Gln Trp Ser Lys His
            100                 105                 110

Pro Leu Thr Phe Gly Ser Gly Thr Lys Val Glu Ile Lys Arg Thr Val
        115                 120                 125

Ala Ala Pro Ser Val Phe Ile Phe Pro Pro Ser Asp Glu Gln Leu Lys
    130                 135                 140

Ser Gly Thr Ala Ser Val Val Cys Leu Leu Asn Asn Phe Tyr Pro Arg
145                 150                 155                 160

Glu Ala Lys Val Gln Trp Lys Val Asp Asn Ala Leu Gln Ser Gly Asn
                165                 170                 175

Ser Gln Glu Ser Val Thr Glu Gln Asp Ser Lys Asp Ser Thr Tyr Ser
            180                 185                 190

Leu Ser Ser Thr Leu Thr Leu Ser Lys Ala Asp Tyr Glu Lys His Lys
        195                 200                 205

Val Tyr Ala Cys Glu Val Thr His Gln Gly Leu Ser Ser Pro Val Thr
    210                 215                 220

Lys Ser Phe Asn Arg Gly Glu Cys
225                 230

<210> SEQ ID NO 9
<211> LENGTH: 1407
<212> TYPE: DNA
<213> ORGANISM: Artificial Sequence
<220> FEATURE:
<223> OTHER INFORMATION: Oligonucleotide

<400> SEQUENCE: 9
atgggatgga gctgtatcat cctcttcttg gtagcaacag ctacaggtgt acacagccag     60
gtgcagctgg tgcagtctgg ggctgaggtg aagaagcctg gggcctcagt gaaggtttcc    120
tgcaaggcat ctggttactc attcactggc tacaccatga actgggtgaa gcaggcccct    180
ggacaagggc ttgagtggat tggacttatt actccttaca atggtgcttc tagctacaac    240
cagaagttca ggggcaaggc caccatgacc agggacacgt ccacgagcac agtctacatg    300
gagctgagca gcctgagatc tgaggacacg gccgtgtatt tctgtgcgag agggggttac    360
gacgggaggg ttttgactac tggggatccg ggaccccggt caccgtctcc tcagcctcc     420 accaagggcc catcggtctt ccccctggca ccctcctcca agagcacctc tgggggcaca    480
gcggccctgg gctgcctggt caaggactac ttccccgaac cggtgacggt gtcgtggaac    540
tcaggcgccc tgaccagcgg cgtgcacacc ttcccggctg tcctacagtc ctcaggactc    600
tactccctca gcagcgtggt gaccgtgccc tccagcagct gggcaccca gacctacatc     660 tgcaacgtga atcacaagcc cagcaacacc aaggtggaca agaaagttga gcccaaatct    720
tgtgacaaaa ctcacacatg cccaccgtgc ccagcacctg aactcctggg gggaccgtca    780
gtcttcctct tccccccaaa acccaaggac accctcatga tctcccggac ccctgaggtc    840
acatgcgtgg tggtggacgt gagccacgaa gaccctgagg tcaagttcaa ctggtacgtg    900
gacggcgtgg aggtgcataa tgccaagaca agccgcggg aggagcagta caacagcacg     960
taccgtgtgt cagcgtcct caccgtcctg caccaggact ggctgaatgg caaggagtac    1020
aagtgcaagg tctccaacaa agccctccca gcccccatcg agaaaaccat ctccaaagcc    1080
```

```
aaagggcagc cccgagaacc acaggtgtac accctgcccc catcccggga tgagctgacc    1140
aagaaccagg tcagcctgac ctgcctggtc aaaggcttct atcccagcga catcgccgtg    1200
gagtgggaga gcaatgggca gccggagaac aactacaaga ccacgcctcc cgtgctggac    1260
tccgacggct ccttcttctt atattcaaag ctcaccgtgg acaagagcag gtggcagcag    1320
gggaacgtct tctcatgctc cgtgatgcat gaggctctgc acaaccacta cacgcagaag    1380
agcctctccc tgtctcccgg gaaatga                                        1407
```

```
<210> SEQ ID NO 10
<211> LENGTH: 468
<212> TYPE: PRT
<213> ORGANISM: Artificial Sequence
<220> FEATURE:
<223> OTHER INFORMATION: Synthetic Construct

<400> SEQUENCE: 10
```

```
Met Gly Trp Ser Cys Ile Ile Leu Phe Leu Val Ala Thr Ala Thr Gly
1               5                   10                  15

Val His Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Ser Phe
        35                  40                  45

Thr Gly Tyr Thr Met Asn Trp Val Lys Gln Ala Pro Gly Gln Gly Leu
    50                  55                  60

Glu Trp Ile Gly Leu Ile Thr Pro Tyr Asn Gly Ala Ser Ser Tyr Asn
65                  70                  75                  80

Gln Lys Phe Arg Gly Lys Ala Thr Met Thr Arg Asp Thr Ser Thr Ser
                85                  90                  95

Thr Val Tyr Met Glu Leu Ser Ser Leu Arg Ser Glu Asp Thr Ala Val
            100                 105                 110

Tyr Phe Cys Ala Arg Gly Gly Tyr Asp Gly Arg Gly Phe Asp Tyr Trp
        115                 120                 125

Gly Ser Gly Thr Pro Val Thr Val Ser Ser Ala Ser Thr Lys Gly Pro
    130                 135                 140

Ser Val Phe Pro Leu Ala Pro Ser Ser Lys Ser Thr Ser Gly Gly Thr
145                 150                 155                 160

Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
            180                 185                 190

Ala Val Leu Gln Ser Ser Gly Leu Tyr Ser Leu Ser Ser Val Val Thr
        195                 200                 205

Val Pro Ser Ser Ser Leu Gly Thr Gln Thr Tyr Ile Cys Asn Val Asn
    210                 215                 220

His Lys Pro Ser Asn Thr Lys Val Asp Lys Lys Val Glu Pro Lys Ser
225                 230                 235                 240

Cys Asp Lys Thr His Thr Cys Pro Pro Cys Pro Ala Pro Glu Leu Leu
                245                 250                 255

Gly Gly Pro Ser Val Phe Leu Phe Pro Pro Lys Pro Lys Asp Thr Leu
            260                 265                 270

Met Ile Ser Arg Thr Pro Glu Val Thr Cys Val Val Val Asp Val Ser
        275                 280                 285

His Glu Asp Pro Glu Val Lys Phe Asn Trp Tyr Val Asp Gly Val Glu
    290                 295                 300
```

```
Val His Asn Ala Lys Thr Lys Pro Arg Glu Glu Gln Tyr Asn Ser Thr
305                 310                 315                 320

Tyr Arg Val Val Ser Val Leu Thr Val Leu His Gln Asp Trp Leu Asn
                325                 330                 335

Gly Lys Glu Tyr Lys Cys Lys Val Ser Asn Lys Ala Leu Pro Ala Pro
            340                 345                 350

Ile Glu Lys Thr Ile Ser Lys Ala Lys Gly Gln Pro Arg Glu Pro Gln
        355                 360                 365

Val Tyr Thr Leu Pro Pro Ser Arg Asp Glu Leu Thr Lys Asn Gln Val
    370                 375                 380

Ser Leu Thr Cys Leu Val Lys Gly Phe Tyr Pro Ser Asp Ile Ala Val
385                 390                 395                 400

Glu Trp Glu Ser Asn Gly Gln Pro Glu Asn Asn Tyr Lys Thr Thr Pro
                405                 410                 415

Pro Val Leu Asp Ser Asp Gly Ser Phe Phe Leu Tyr Ser Lys Leu Thr
            420                 425                 430

Val Asp Lys Ser Arg Trp Gln Gln Gly Asn Val Phe Ser Cys Ser Val
        435                 440                 445

Met His Glu Ala Leu His Asn His Tyr Thr Gln Lys Ser Leu Ser Leu
450                 455                 460

Ser Pro Gly Lys
465

<210> SEQ ID NO 11
<211> LENGTH: 699
<212> TYPE: DNA
<213> ORGANISM: Artificial Sequence
<220> FEATURE:
<223> OTHER INFORMATION: Oligonucleotide

<400> SEQUENCE: 11
atgggatgga gctgtatcat cctcttcttg gtagcaacag ctacaggtgt acacagcgaa      60
attgtgttga cacagtctcc agccaccctg tctttgtctc aggggaaaag agccaccatg     120
acctgcagtg ccagctcaag tgtaagttac atgcactggt accaacagaa acctggccag     180
gctcccaggc tcctcatcta tgacacatcc aaactggctt ctggcgtccc agccaggttc     240
agtggcagtg gtctgggac agacttcact ctcaccatca gcagcctaga gcctgaagat     300
tttgcagttt attactgtca gcagtggagt aagcaccctc tcacgttcgg atccgggacc     360
aaggtggaaa tcaaacgaac tgtggctgca ccatctgtct tcatcttccc gccatctgat     420
gagcagttga aatctggaac tgcctctgtt gtgtgcctgc tgaataactt ctatcccaga     480
gaggccaaag tacagtggaa ggtggataac gccctccaat cgggtaactc ccaggagagt     540
gtcacagagc aggacagcaa ggacagcacc tacagcctca gcagcaccct gacgctgagc     600
aaagcagact acgagaaaca caaagtctac gcctgcgaag tcacccatca gggcctgagc     660
tcgcccgtca caaagagctt caacagggga gagtgttaa                             699

<210> SEQ ID NO 12
<211> LENGTH: 232
<212> TYPE: PRT
<213> ORGANISM: Artificial Sequence
<220> FEATURE:
<223> OTHER INFORMATION: Synthetic Construct

<400> SEQUENCE: 12

Met Gly Trp Ser Cys Ile Ile Leu Phe Leu Val Ala Thr Ala Thr Gly
1               5                   10                  15
```

```
Val His Ser Glu Ile Val Leu Thr Gln Ser Pro Ala Thr Leu Ser Leu
        20                  25                  30

Ser Pro Gly Glu Arg Ala Thr Met Thr Cys Ser Ala Ser Ser Ser Val
        35                  40                  45

Ser Tyr Met His Trp Tyr Gln Gln Lys Pro Gly Gln Ala Pro Arg Leu
50                          55                  60

Leu Ile Tyr Asp Thr Ser Lys Leu Ala Ser Gly Val Pro Ala Arg Phe
65                  70                  75                  80

Ser Gly Ser Gly Ser Gly Thr Asp Phe Thr Leu Thr Ile Ser Ser Leu
                85                  90                  95

Glu Pro Glu Asp Phe Ala Val Tyr Tyr Cys Gln Gln Trp Ser Lys His
            100                 105                 110

Pro Leu Thr Phe Gly Ser Gly Thr Lys Val Glu Ile Lys Arg Thr Val
            115                 120                 125

Ala Ala Pro Ser Val Phe Ile Phe Pro Pro Ser Asp Glu Gln Leu Lys
130                 135                 140

Ser Gly Thr Ala Ser Val Val Cys Leu Leu Asn Asn Phe Tyr Pro Arg
145                 150                 155                 160

Glu Ala Lys Val Gln Trp Lys Val Asp Asn Ala Leu Gln Ser Gly Asn
                165                 170                 175

Ser Gln Glu Ser Val Thr Glu Gln Asp Ser Lys Asp Ser Thr Tyr Ser
            180                 185                 190

Leu Ser Ser Thr Leu Thr Leu Ser Lys Ala Asp Tyr Glu Lys His Lys
            195                 200                 205

Val Tyr Ala Cys Glu Val Thr His Gln Gly Leu Ser Ser Pro Val Thr
        210                 215                 220

Lys Ser Phe Asn Arg Gly Glu Cys
225                 230
```